United States Patent [19]

Levin et al.

[11] Patent Number: 5,724,580

[45] Date of Patent: Mar. 3, 1998

[54] SYSTEM AND METHOD OF GENERATING PROGNOSIS AND THERAPY REPORTS FOR CORONARY HEALTH MANAGEMENT

[75] Inventors: Richard I. Levin, New York, N.Y.; Michael W. Cox, Point Pleasant, N.J.

[73] Assignee: qmed, Inc., Lawrence Harbor, N.J.

[21] Appl. No.: 822,177

[22] Filed: Mar. 20, 1997

Related U.S. Application Data

[63] Continuation of Ser. No. 414,510, Mar. 31, 1995, abandoned.

[51] Int. Cl.⁶ ............................................. G06F 17/30
[52] U.S. Cl. ...................... 395/615; 395/202; 395/203; 128/670; 128/695 R; 128/702
[58] Field of Search .............................. 395/202, 203, 395/615, 670, 702

[56] References Cited

U.S. PATENT DOCUMENTS

| Re. 33,834 | 3/1992 | Warner | 128/670 |
|---|---|---|---|
| 4,290,114 | 9/1981 | Sinay | 364/413.02 |
| 4,315,309 | 2/1982 | Coli | 364/413.02 |
| 4,347,851 | 9/1982 | Jundanian | 128/668 |
| 4,610,254 | 9/1986 | Morgan et al. | 128/696 |
| 4,679,144 | 7/1987 | Cox et al. | 364/413.02 |
| 4,834,107 | 5/1989 | Warner | 128/696 |
| 4,893,270 | 1/1990 | Beck et al. | 364/400 |
| 4,945,477 | 7/1990 | Edwards | 364/413.06 |
| 4,957,115 | 9/1990 | Selker | 128/696 |
| 4,974,162 | 11/1990 | Seigel et al. | 364/413.02 |
| 4,998,535 | 3/1991 | Selker et al. | 128/696 |
| 5,007,429 | 4/1991 | Treach et al. | 128/677 |
| 5,018,067 | 5/1991 | Mohlenbrock et al. | 364/413.02 |
| 5,046,499 | 9/1991 | Berger | 128/654 |
| 5,199,439 | 4/1993 | Zimmerman et al. | 128/670 |
| 5,262,943 | 11/1993 | Thibado et al. | 364/413.01 |
| 5,265,010 | 11/1993 | Evan-Paganelli et al. | 364/413.02 |
| 5,276,612 | 1/1994 | Selker | 364/413.06 |
| 5,277,188 | 1/1994 | Selker | 128/696 |
| 5,301,105 | 4/1994 | Cummings, Jr. | 364/401 |
| 5,307,263 | 4/1994 | Brown | 364/413.09 |
| 5,370,122 | 12/1994 | Kunig et al. | 128/670 |
| 5,392,210 | 2/1995 | Scholz | 364/413.01 |
| 5,396,886 | 3/1995 | Cuypers | 128/630 |
| 5,416,695 | 5/1995 | Stutman et al. | 364/413.02 |
| 5,437,285 | 8/1995 | Verrier et al. | 128/702 |
| 5,471,382 | 11/1995 | Tallman et al. | 364/406 |
| 5,474,050 | 12/1995 | Begun et al. | 128/707 |
| 5,492,117 | 2/1996 | Eisenberg et al. | 128/696 |
| 5,501,229 | 3/1996 | Selker et al. | 128/696 |
| 5,626,144 | 5/1997 | Tacklind et al. | 128/725 |

*Primary Examiner*—Thomas G. Black
*Assistant Examiner*—Hosain T. Alam
*Attorney, Agent, or Firm*—John R. Mugno

[57] ABSTRACT

A system and method of automatically formulating an alpha-numeric comprehensive management and prognosis report at a centralized data management center for a patient at a remote location is defined comprising: means for converting information regarding the condition of the patient into data; a first telecommunications means for transferring data to the centralized data management center; and processing means at the centralized data management center for receiving the data and for generating the comprehensive management and prognosis report based on analysis of the data. A storage means is also provided at the centralized data management center for maintaining a record of the data received by and transmitted from the centralized data management center in a relational data base format.

24 Claims, 28 Drawing Sheets

OHMS / CAD LIPID ALGORITHM

OHMS / CAD SMOKING CESSATION ALGORITHM

OHMS / CAD OBESITY ALGORITHM

Dear Doctor Jasim Al Jawad:

The following report on                                        will provide you with recommendations for his current and ongoing coronary management.

Mr. Joseph Parato's ambulatory ischemia results were positive.

ANTIISCHEMIC THERAPY
Monitor One STRx detected 272 minute(s) of ambulant ST segment deviation when        wore the system on March 13 and March 14, 1995. Available data indicate that this result places him in the highest risk category for a cardiac event in the next year. Consultation with our cardiology service and/or your local cardiologist is urged in order to select the best therapeutic strategy.

LIPID PROFILE
Our records do not include any data on the lipid levels of patient        Since lipids are a major modifiable risk factor for CAD and its complications, we recommend obtaining LDL, HDL, and triglyceride levels before the patient's next ischemia monitoring with Monitor One STRx. If these values are currently known, please report them to us.

ANTIHYPERTENSIVE THERAPY
According to our records,        has a BP of 150 / 85. This is MILD HYPERTENSION (Stage 1) according to the classification of the Joint National Committee on Detection, Evaluation, and Treatment of High Blood Pressure. He should be encouraged to achieve an ideal body weight, refrain from excessive alcohol intake, participate in a regular exercise regimen, reduce sodium intake and stop smoking. Our records indicate that drug(s) with an antihypertensive effect currently being administered are: nifedipine 90.000 mg taken QD and ramipril 5.000 mg taken QD . If this is the current therapy, we recommend the following: because        has ambulant ischemia in addition to elevated blood pressure, we ask that you contact our cardiology service at ohms center. He should be seen again to determine response to therapy and the presence of adverse effects within a month. Subsequent adjustments in therapy to reach the target BP of 120/80 should be made at 1-3 month intervals.

ANTITHROMBOTIC THERAPY
According to our records,        is currently taking 325.000 mg of aspirin QD. We recommend maintenance of this regimen.

ANTITHROMBOTIC THERAPY
According to our records,        is not currently taking aspirin and there is no contraindication to aspirin therapy. If these records are correct and since aspirin has been shown to be useful for the prevention of cardiac events, we recommend that a formulation of aspirin between 80 mg and 325 mg should be administered daily or every other day.

DIABETES
Our records show that        is not diabetic and no glucose level is reported. Optimal glucose control may reduce the risk of complications of CAD in patients with DM and adults may develop diabetes at any

FIG. 25A time. Therefore, please report the glucose level to us if it is known or obtain a fasting glucose level prior to the next monitoring session.

SMOKING CESSATION
Our records show that          is currently smoking. If this is true and because smoking is a major modifiable risk factor for CAD and its complications, every effort should be made to help the patient stop smoking. Counseling, behavioral modification and nicotine patch therapy should be considered. Even if such efforts have been made in the past, they should be made again.

IDEAL BODY WEIGHT
Our records show that patient          is not currently at ideal body weight with a weight of 220 pounds and a height of 66 inches. ohms recommends a program of regular exercise coupled with a diet such as the Step 1 NCEP diet for this patient.

PROGRAM OF REGULAR EXERCISE
Our records show that          is not currently engaged in a program of regular exercise. A program of regular exercise has been shown to reduce the risk of death and disability from CAD and should therefore be recommended.

If you have any questions about these recommendations, please feel free to call the ohms center to discuss this report with our cardiology service.

Very truly yours,

Richard I. Levin, M.D. FACC

FIG. 25B

SYSTEM AND METHOD OF GENERATING PROGNOSIS AND THERAPY REPORTS FOR CORONARY HEALTH MANAGEMENT

This application is a continuation of application Ser. No. 08/414,510 filed on Mar. 31, 1995, now abandoned.

FIELD OF INVENTION

This invention is generally directed to the field of the diagnosis, treatment and prognosis for patients with coronary disease, and more particularly, to the formulation of a preferred written coronary treatment regimen which is based on an algorithm which utilizes transferred data which is reflective of a particular patient's physical condition. The algorithm, which is based on previously identified risk factors and prior treatment of the patient, can automatically generate a recommended written regimen, thus resulting in an expeditious and accurate prognosis report.

BACKGROUND OF THE INVENTION

Despite significant advancements in treatment, coronary artery disease remains the leading cause of death in the United States of America. The death rate for coronary artery disease remains high due to the fact that it remains difficult to predict which asymptomatic individuals or patients will suffer massive heart attacks resulting in death. While it is known that persons who have previously suffered heart attacks are at a greater risk of death, many persons have fatal heart attacks with no known previous symptoms of heart disease such as angina pectoris.

As recited in U.S. Pat. No. 4,679,144, which is owned by the assignee of the present invention, qmed, inc., of New Jersey, a deviation of the ST segment of an electrocardiographic (ECG) signal can be a very effective predictor of which patients are at significant risk of suffering myocardial infarction and/or sudden death. Recent research has supported the value of detecting "silent" ST segment deviation. The apparatus disclosed in the '144 patent permits real-time monitoring of the ECG signal, including, in particular, ambulatory or ambulant detection of deviations in the ST segment. Storage of such ECG data is also possible. A portable apparatus incorporating the teachings of the '144 patent is now sold by qmed, inc. under the trademark MONITOR ONE®. The preferred embodiment of the present invention which will be described hereinafter will utilize deviation of the ST segment as a primary predictor of those patients at a significant risk of coronary events (i.e., unstable angina, myocardial infarction and sudden death).

One advantage of utilizing ST segment deviation as an important indicator of risk is a reduction in the inappropriate and unnecessary use of invasive procedures. Since the current invention will accurately stratify patients into groups needing invasive procedures and groups needing other therapies the number of invasive procedures will decline. Furthermore, the lay public has the misimpression that bypass surgery, angioplasty and/or atherectomy are curative. These procedures are largely, if temporarily, successful in relieving angina but they are certainly not curative. Studies have proven that angina returns at a progressive rate after bypass surgery. Furthermore, with angioplasty and atherectomy, repeat procedures are frequently required within the first year due to primary failure or restenosis. In conclusion, while invasive procedures provide temporary relief of angina, they are extremely costly, of variable curative value, and not an appropriate alternative for all patients.

Obviously, one of the best means of achieving advancements in any field of medicine is the sharing of information by doctors by means of consultations, case studies, or more broadly stated, the sharing of previously gathered experience. This sharing of information to provide advancements in treatment therapies for a particular field of medicine often takes the form of meetings, seminars or the publication of reports in well-respected medical journals. The problems with such oral or written reports include both their limited nature (i.e., a doctor rarely reports on every case) and inaccuracies or omissions in reporting or interpreting such cases. Even if all information were properly disseminated, another problem is ensuring that such information becomes known to the medical personnel actually treating a patient with a specific malady.

A worldwide effort is presently underway to decrease spiraling medical costs. One result of this effort to decrease costs is the increased use of health management organizations. The goal of such organizations is to "filter" all patients through less expensive primary care physicians before a patient is referred to more costly specialists. Thus, the primary care physician necessarily needs to become a broader generalist. At the same time, it is even more critical that the most advanced information pertinent to specific illnesses (such as coronary artery disease) be made available to the primary care physician. Unfortunately, the most common route of coronary therapy utilized by to the primary care physician is simply to refer the patient to a specialist. The primary care physicians is, in general, ill equipped to deliver optimal coronary care and the is no mechanism to educate and assist him/her in the specific management of each unique patient with coronary disease. Thus, it can be appreciated that the prior art does not provide a fast, real-time, effective technique for providing a comprehensive report for the management of coronary patients based on individual signs and risk factors, and which utilizes all known information both of that particular patient and the patient pool in general.

It is therefore an object of the present invention to provide a new and improved system and method for the management of coronary illness which provides fast and accurate treatment strategies based on up-to-date information of both the particular patient undergoing treatment and the latest known treatment data in general.

It is still another object of the present invention to provide a new and improved system and method for the determination of treatment and prognosis of coronary illness which minimizes the use of invasive procedures.

It is still another object of the present invention to provide a new and improved system and method for the determination of treatment and prognosis of coronary illness which permits the correlation and analysis of data on a large group of patients studied repeatedly over their remaining lifetimes in order to evaluate the accuracy of diagnoses, prognosis, and effectiveness of various recommended treatment strategies.

Further objects and advantages of the present invention will become apparent as the following description proceeds.

SUMMARY OF THE INVENTION

Briefly stated and in accordance with a preferred embodiment of the present invention, a system and method of automatically formulating an alpha-numeric comprehensive management and prognosis report at a centralized data management center for a patient at a remote location is defined comprising: means for converting information regarding the condition of the patient into transferable data; a first telecommunications means for transferring data to the centralized data management center; and processing means at the centralized data management center for receiving the data and for generating the comprehensive management and prognosis report based on analysis of the data. A storage means is also provided at the centralized data management center for maintaining a record of the data received by and transmitted to the centralized data management center organized as a relational database.

BRIEF DESCRIPTION OF THE DRAWINGS

While the specification concludes with claims particularly pointing out and distinctly claiming the subject matter regarded as the invention herein, it is believed that the present invention will be more readily understood upon consideration of the following description taken in conjunction with the accompanying drawings, wherein:

FIGS. 25A and 25B represent a sample alpha-numeric comprehensive management and prognosis report for a coronary patient in accordance with the present invention.

DETAILED DESCRIPTION OF THE DRAWINGS

Figure 1:
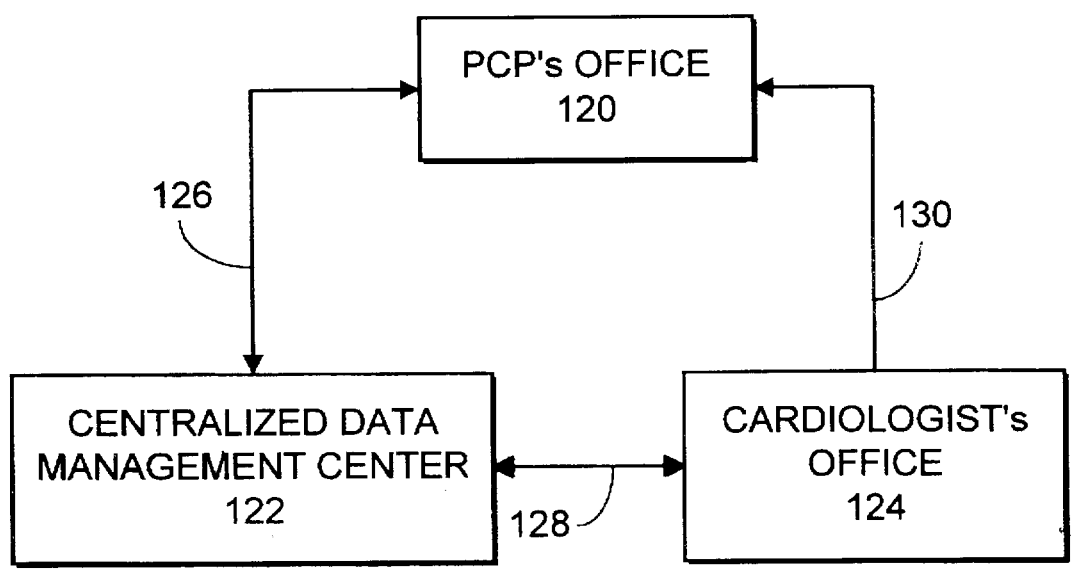
FIG. 1 is a basic block illustration of the communication flow between various sites as implemented in the present invention.

Referring first to FIG. 1, the general flow of information between a primary care physician's office 120, a centralized data management center 122, and a cardiologist's office 124 is described. It should be noted that information (typically in the form of digital data) can be provided in either direction between both primary care physician's office 120 and centralized data management center 122, and between centralized data management center 122 and cardiologist's office 124. Thus, communications lines 126 and 128 indicate arrows in both directions. Alternatively, a communication line 130 between primary care physician's office 120 and cardiologist's office 124 only permits communication in the direction from office 124 to office 120. This limitation to the communication of data is to permit centralized data management center 122 to properly correlate all information and recommended therapies for further study. Moreover, communication line 130 is drawn in shadow since in most instances it would be desirable for the diagnosis and treatment recommendations from cardiologist's office 124 to first pass back through centralized data management center 122 before being relayed onto the primary care physician's office 120. Again, this restricted flow of information permits storage of empirical data at centralized data management center 122.

It should be noted that office 120 has been described as belonging to a primary care physician simply for purposes of explanation. Certainly, the remote primary care physician's office 120 can actually be a cardiologist or any type of physician. Thus, in effect a communication loop represented in FIG. 1 can represent communications between doctors practicing within the same field.

Referring next to FIG. 2, once again primary physician's office 120, centralized data management center 122, and specialist's office 124 are illustrated in block format. However, additional components which are implemented when incorporating the present invention are also described. General information such as doctor's ID number, patient's assigned ID number, birth date, sex, height, weight, coronary status, blood pressure, known allergic conditions, cholesterol levels, glucose levels, present drug regimens, smoking habits and exercise regimes are input into a hand-held monitor 132. Monitor 132 is preferably menu driven to insure that the medical personnel at primary physician's office 120 enters all known and required information. Monitor 132 is also capable of storing either real-time ECG information or ECG information which has been stored for the past 24–48 hours. Such information is acquired by connecting monitor 132 to the patient by means of leads 133. Where real-time information is being gathered, it may be desirable under particular circumstances to connect leads 133 to the patient while a stress test is being conducted.

Once all known information has been input into monitor 132, it is placed onto buffer interface module (BIM) 134. BIM 134 is optionally used for convenience of the user and is capable of converting the data received from monitor 132 into a format suitable for transmission over a telephone line. For instance, all known drugs are assigned an identifying code. The information relating to the patient's condition is then transmitted from modem 136, along communication line 138, to centralized data management 122.

Figure 2:
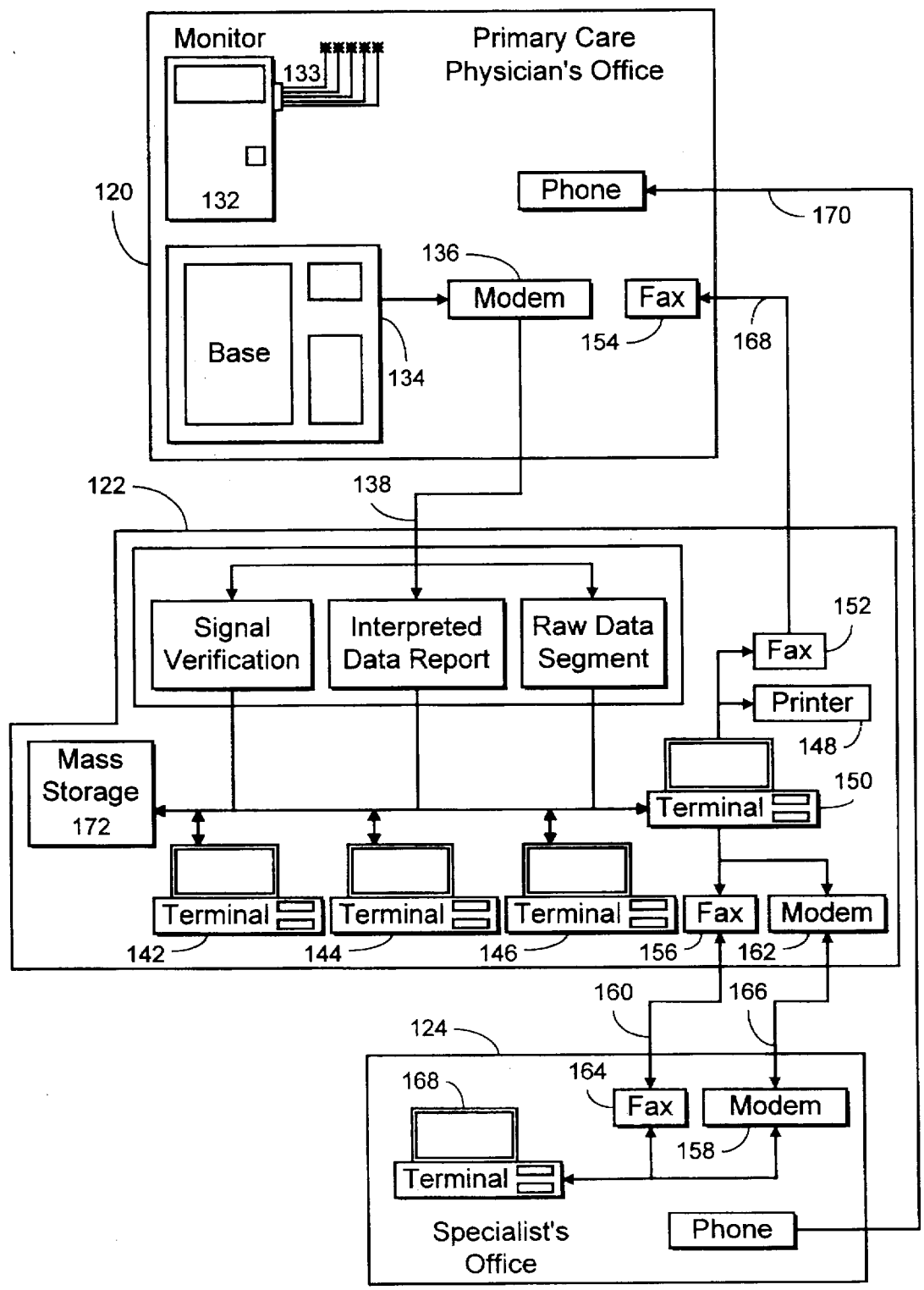
FIG. 2 is a schematic block diagram of the present invention providing for communication between a primary care physician's office, a centralized data management center, and a specialist's office.

Box 140 can indicate a microprocessor which verifies proper receipt of the data from communication line 138, interprets the data, and maintains in storage the raw data segments. In FIG. 2, each of these steps is indicated by separate boxes 143, 145, and 147 and forwarded to separate terminals numbered 142, 144 and 146. It should be understood that a single terminal can be substituted for this more complex arrangement. The software run in computer 140 will be described in greater detail herein but, in general terms, it uses the data in several algorithms and ultimately provides an alpha-numeric printout representing the desired comprehensive report and course of treatment.

The recommended treatment therapy can be printed out at a printer 148, which is connected to a terminal 150. This printed message can be forwarded via facsimile from a facsimile machine 152 at centralized data management center 124 to a facsimile machine 154 at primary care physician's office 120. Once again, it should be noted that printer 148, terminal 150 and facsimile 152 are optional, and instead their functions can be carried out completely within computer 140 by means of an internal fax as an example. FIG. 2 has been described in greater detail to permit an easier understanding by non-technical practitioners.

When it is desirable to consult specialist's office 124 before generating the alpha-numeric comprehensive management and prognosis report or when it is necessary to confirm the written report, information can be transmitted either from facsimile machine 156, via a communication line 160, to a facsimile machine 158, or alternatively, from a modem 162, via communication line 166, to a modem 164. The specialist at office 124 can then review information on a terminal 168, which may simply be displaying data in computer 140, to help establish a comprehensive management and prognosis report or to ensure that a proper report has been generated. If the report is altered in any way, it is desirable that the modified report be transferred back to centralized data management center 122, through either communication line 160 or 166, and then to primary care physician's office 120 through communication line 168. This will ensure that all reports are known at centralized data management center 122. Alternatively, in urgent situations, the cardiologist can call the primary care physician over a communication line 170. Each of the communication lines described herein are typically a standard telephone line.

Significantly, terminal 150 which maintains information regarding the data, diagnosis, and recommended prognosis reports, is connected to a storage means 172. Storage means 172 will permit physicians to accurately determine the effectiveness of diagnoses and treatments as such information is gathered over the course of time and as the pool of treated patients increases. This information can be made available to doctors on the network. It is hoped that this information will be used to effectively identify patients at significant risk of sudden death and to quantify the success of various treatments both for the patient pool in general and for particular patients. Periodic reviews of this information will permit further modifications to the software to make it more effective in treating patients.

Figure 3:
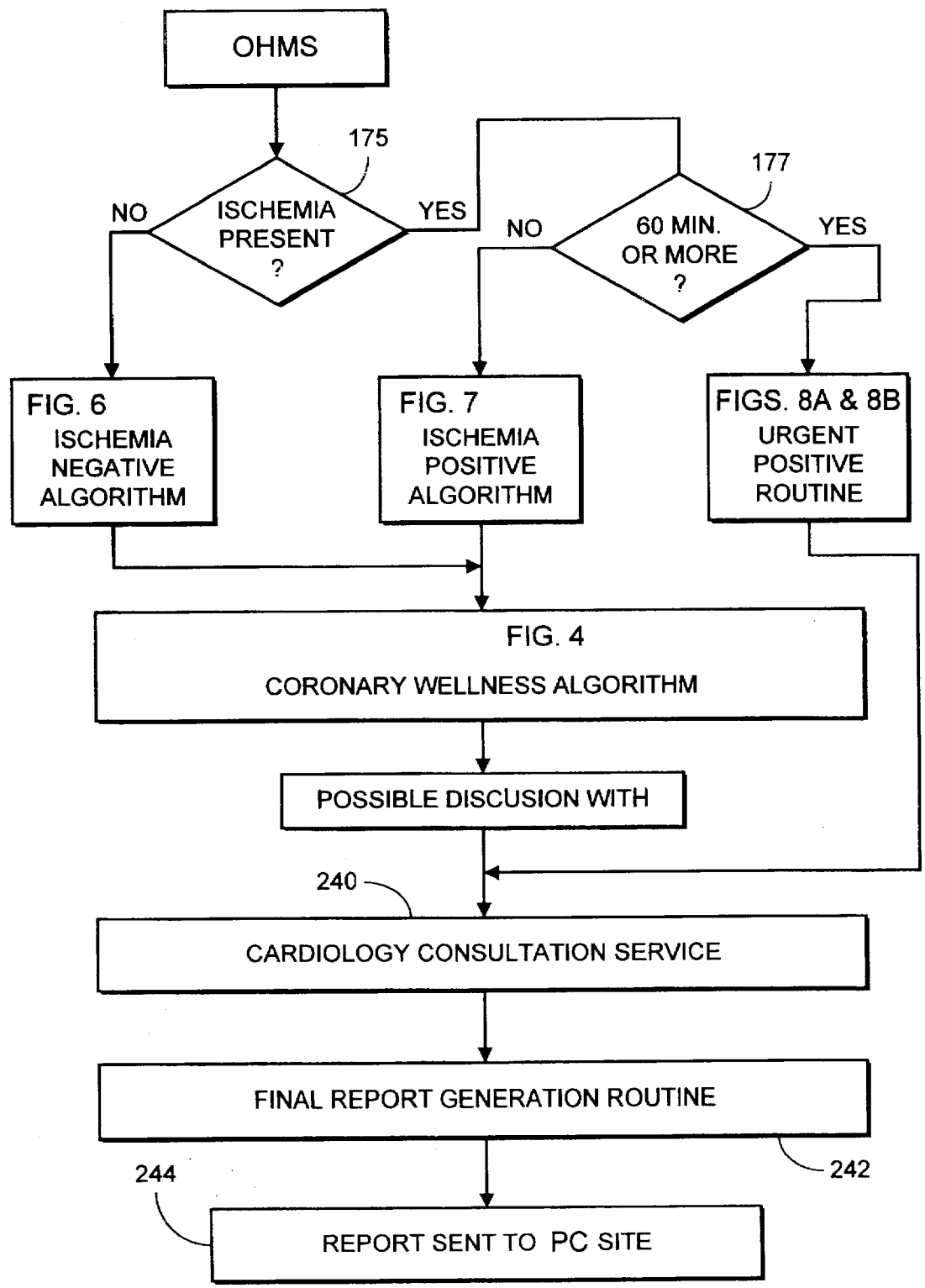
FIG. 3 is a block flow diagram of a master clinical algorithm used in a preferred embodiment of the present invention wherein the detection of ischemia is the predominant factor used to determine additional case management for a patient.

FIG. 3 represents a block flow diagram of a master clinical algorithm of a best mode embodiment of the present invention and is representative of the software run in computer 140. After the patient information from monitor 132 is downloaded into buffer interface module 134, and the medical data is converted into information suitable for transmission, it is transmitted to centralized data management center 122. The master clinical algorithm of FIG. 3 is then run. Box 173, which is labeled "OHMS" stands for "on-line health management system". This box simply represents the start box of the master clinical algorithm of FIG. 3.

Figure 6:
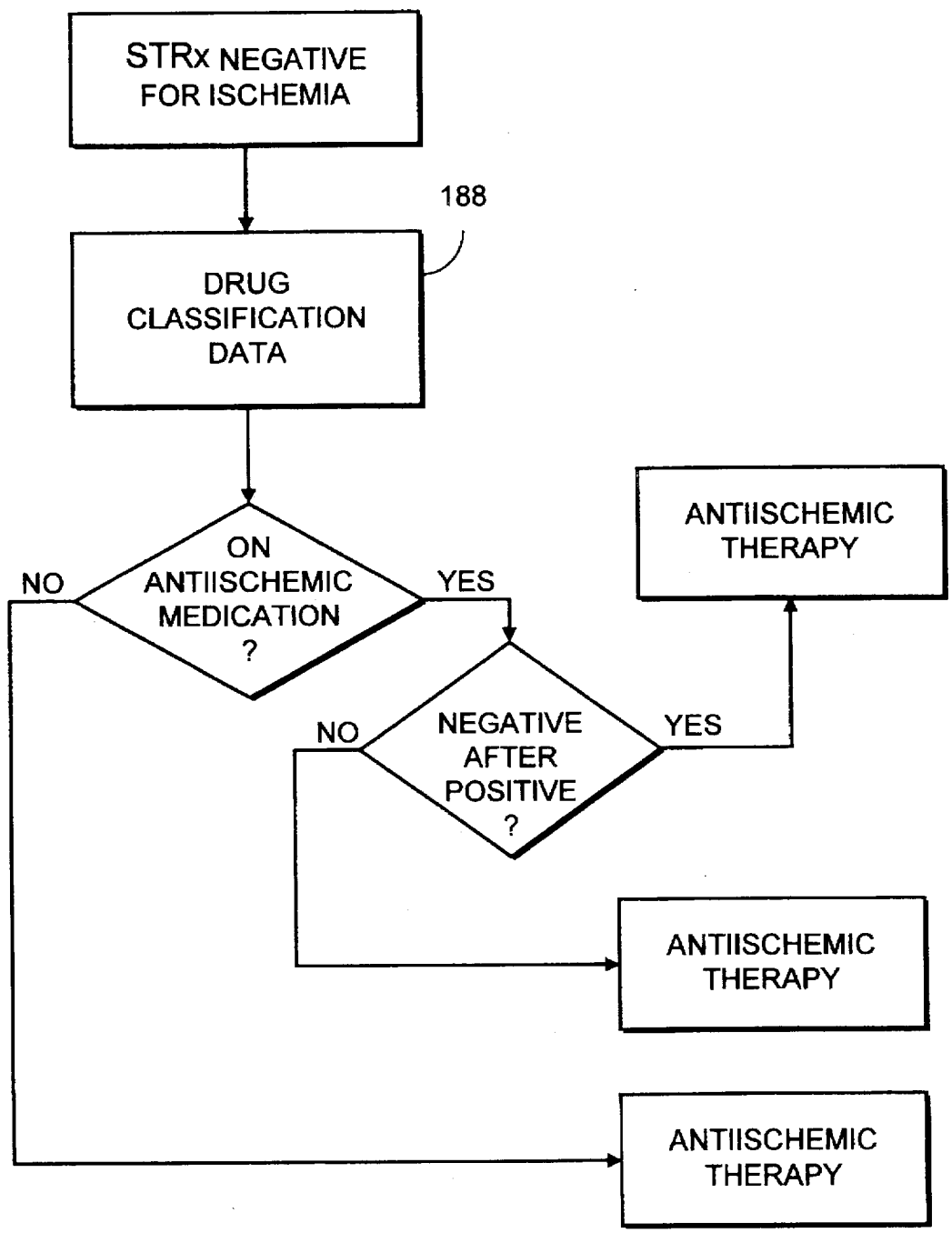
FIG. 6 is a negative ischemia algorithm used in conjunction with the preferred embodiment of the present invention.
Figure 7:
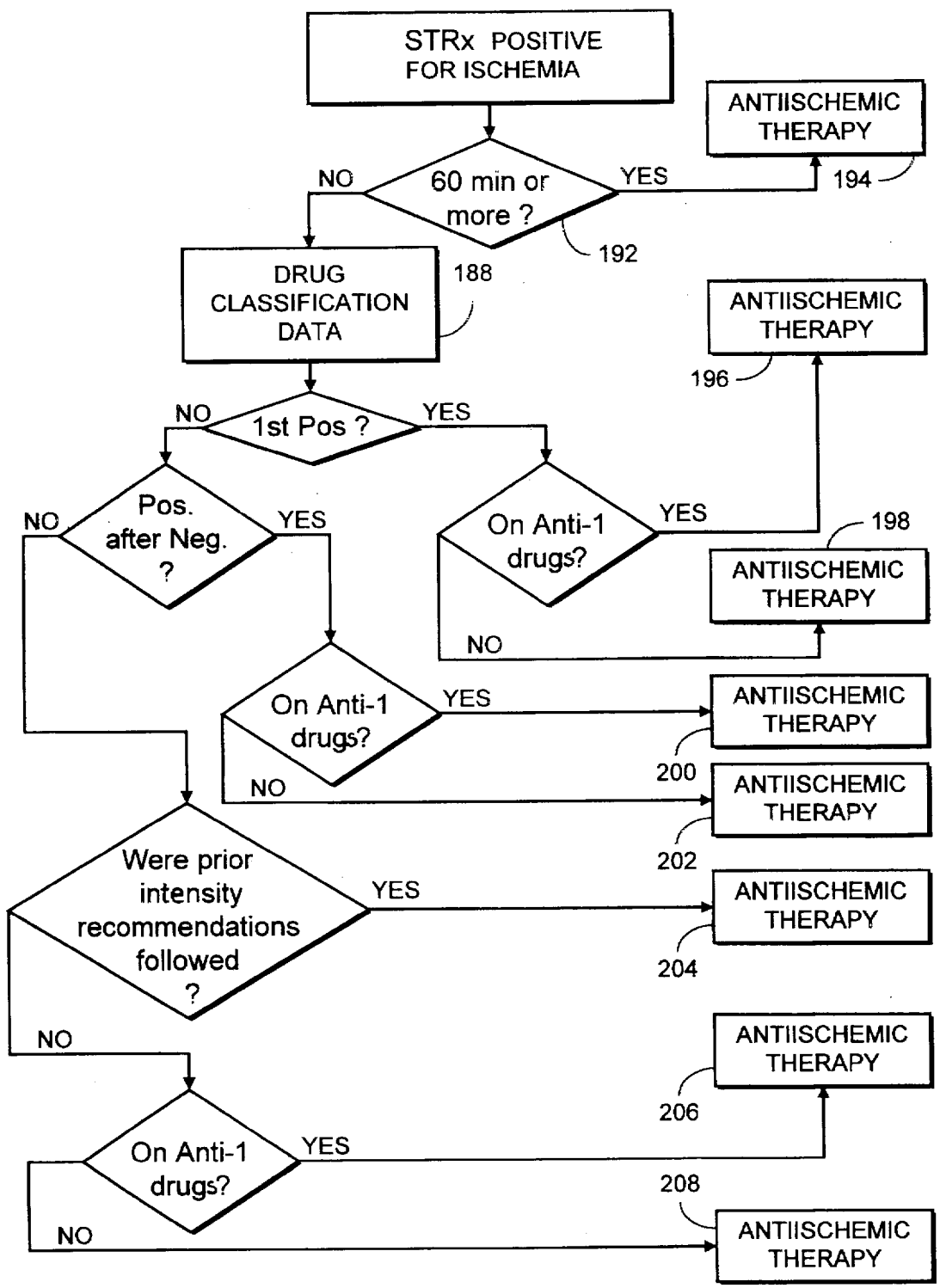
FIG. 7 is a block flow diagram of a positive ischemia algorithm used in conjunction with the preferred embodiment of the present invention.
Figure 8A:
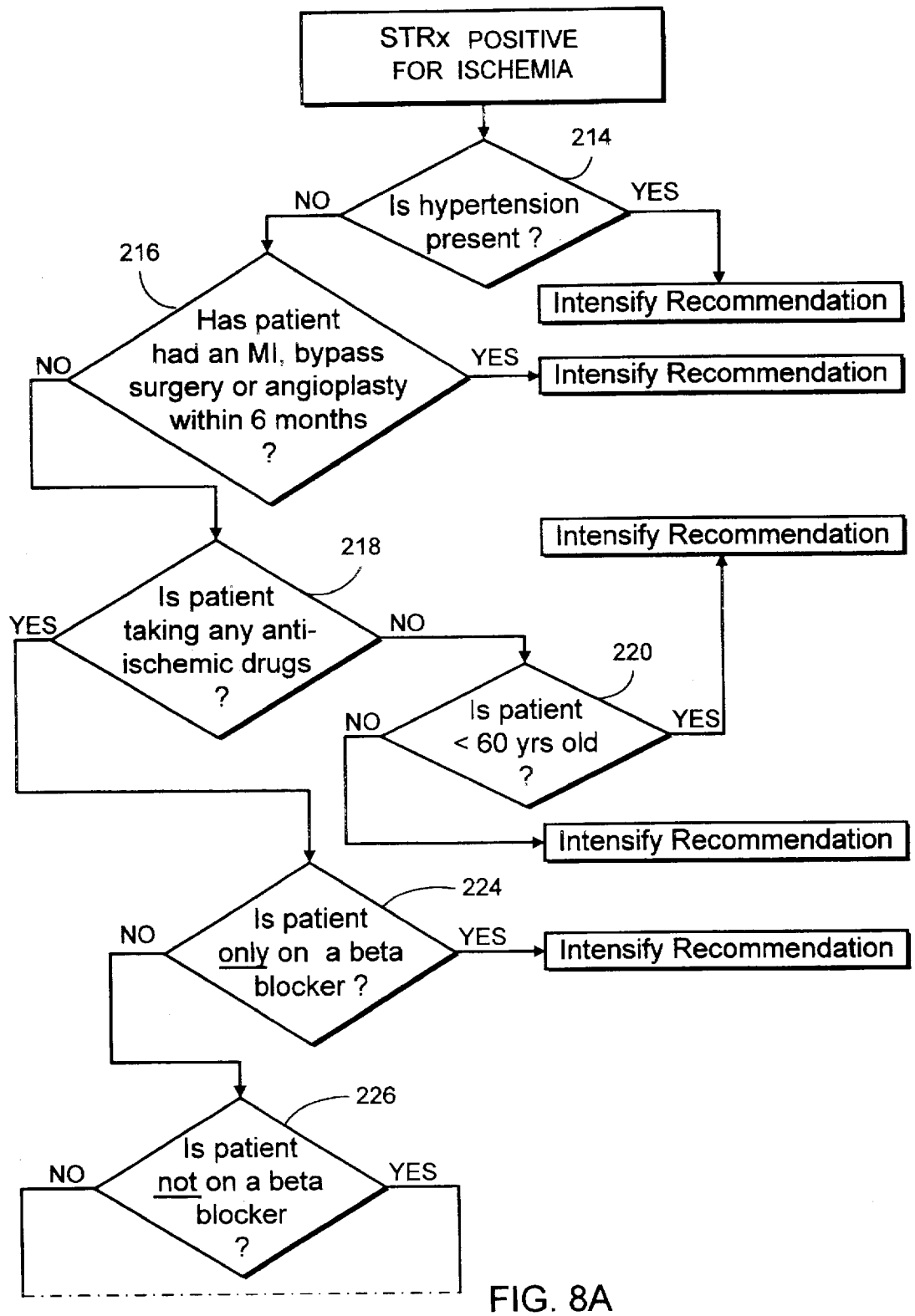
FIGS. 8A and 8B represent a block flow diagram of an urgent positive ischemia algorithm used in conjunction with the preferred embodiment of the present invention.
Figure 8B:
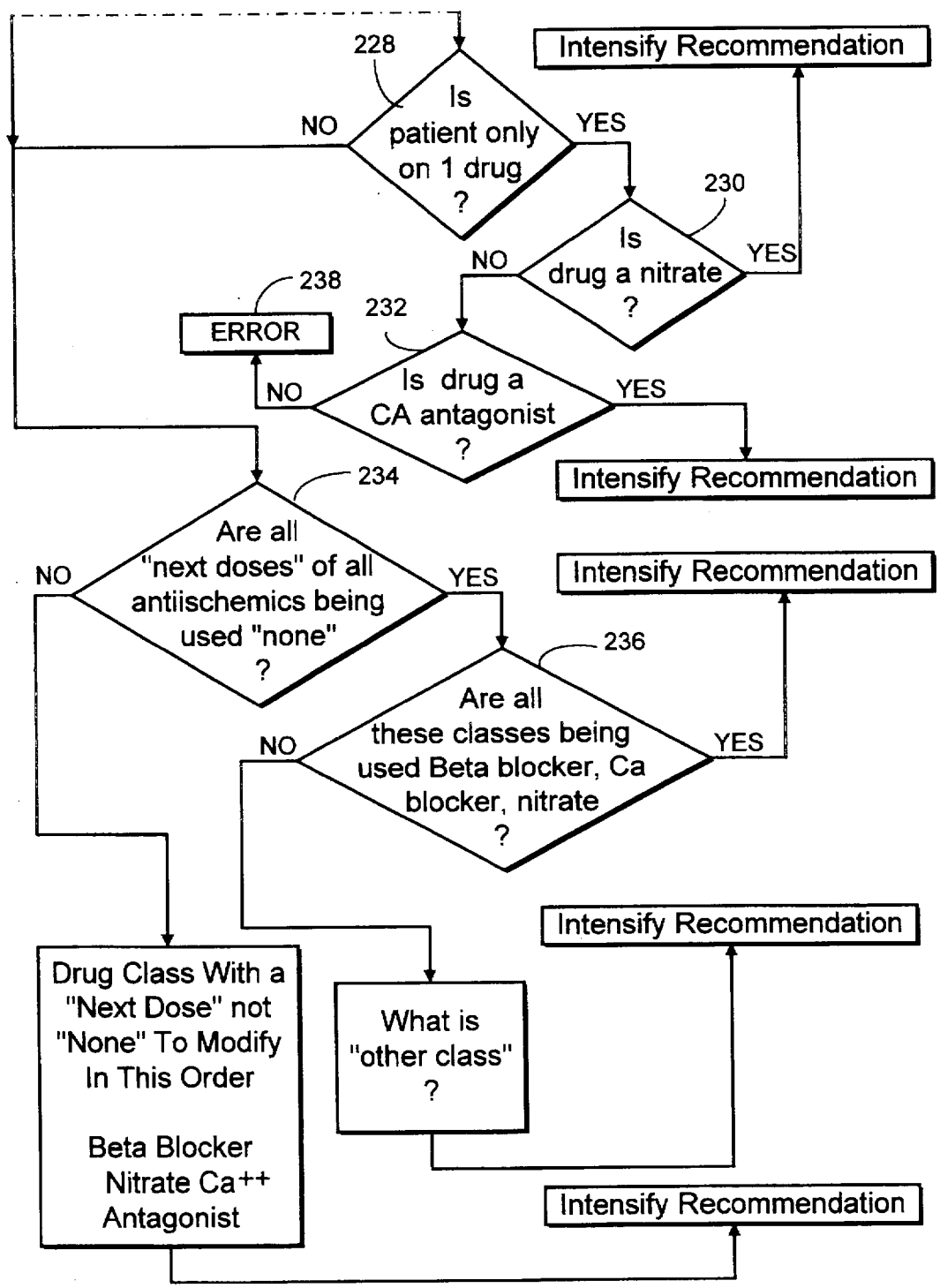

At decision box 175, it is determined whether ischemia is present. If ischemia is not detected, the negative ischemia algorithm of FIG. 6 is run. Alternatively, if ischemia is present, a determination is made (box 177) whether ischemia has been present for more than 60 minutes. If the detected ischemia has been present for less than 60 minutes, the positive ischemia algorithm of FIG. 7 is run. Alternatively, if ischemia has been present for more than 60 minutes, the urgent positive ischemia routine of FIGS. 8A and 8B are run.

The first possibility to be considered is when no ischemia is present. The first determination to be made by the algorithm of FIG. 6 is to determine and classify any drugs the patient may presently be taking. This determination is made by reference to the drug classification algorithm of FIG. 5. In box 190 of FIG. 5, it can be seen that there are ten categories and corresponding classifications of drugs. Those drugs deemed antischemic are beta blockers, calcium channel blockers, and nitrates. Of course, the box 190 listing of drugs can be enhanced as desired by the user.

Once the drug classification data has been determined by box 188, one of various therapies will be recommended. These antischemic therapies will take the form of a written comprehensive management and prognosis report. The report may advise commencing, increasing, or decreasing medications.

Figure 4:
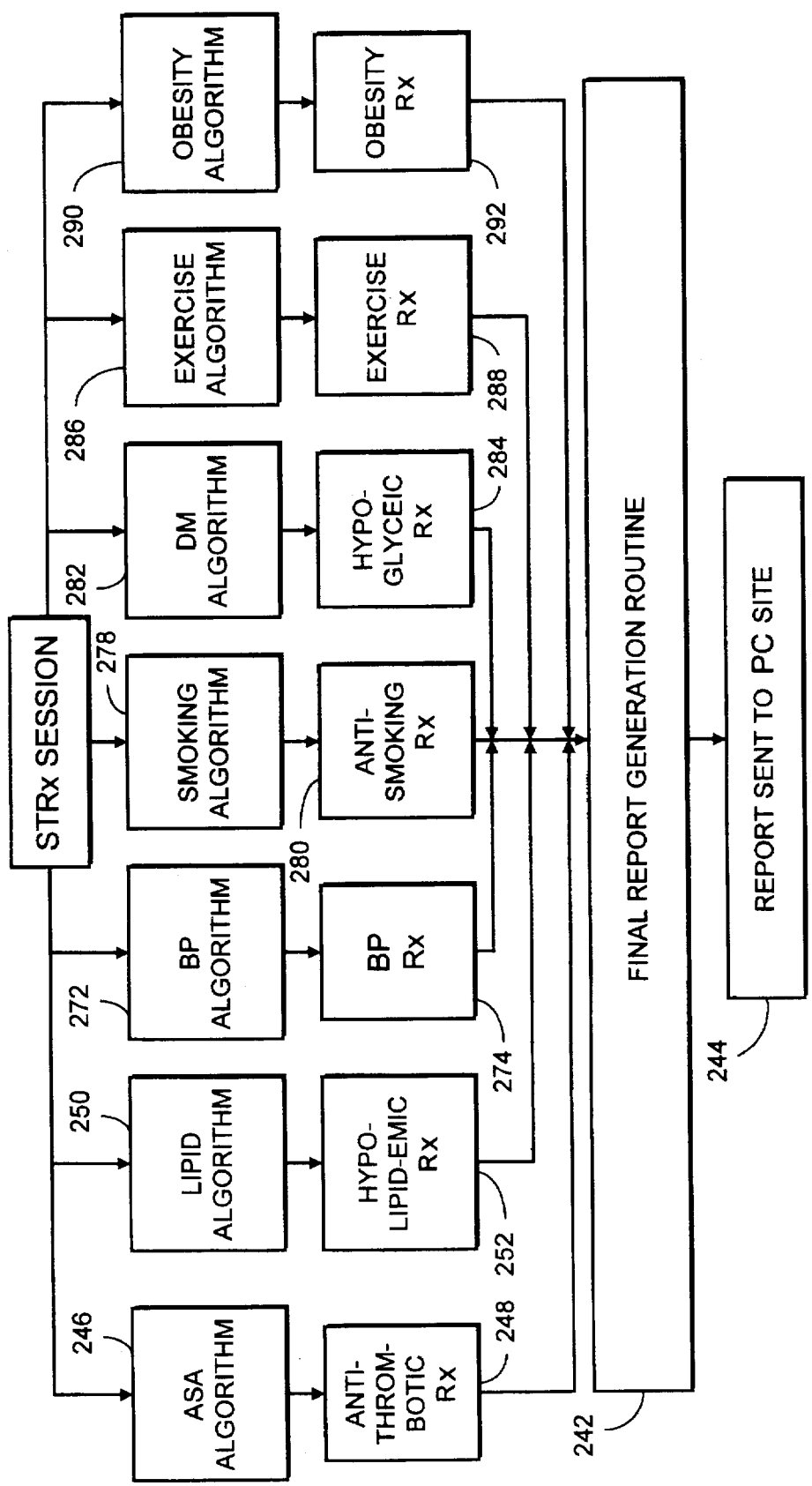
FIG. 4 is a block flow diagram of a coronary wellness master algorithm used in conjunction with the preferred embodiment of the present invention.

Referring back to FIG. 3, once the negative ischemia algorithm has been run, the coronary wellness master algorithm of FIG. 4 will be commenced. This coronary wellness master algorithm will be described after the description of the algorithms of FIG. 7 (positive ischemia algorithm) and FIGS. 8A and 8B (urgent positive ischemia algorithm).

Turning to FIG. 7, although not necessary, the algorithm will once again check if ischemia has been present for more than 60 minutes (box 192). If so, the antischemic therapy of box 194 will be printed and recommended to the attending physician. If not, once again, the drug classification data algorithm 188 (FIG. 5) is run, or at least, the results of this previously run algorithm are recalled.

As can be easily ascertained from a quick review of FIG. 7, different antischemic therapies 196, 198, 200, 202, 204, 206 or 208 are printed depending on factors relating to whether this is the patient's first positive result for ischemia, whether the patient previously has been prescribed antischemic drugs, or whether previous recommended drug therapies have been followed.

Figure 5:
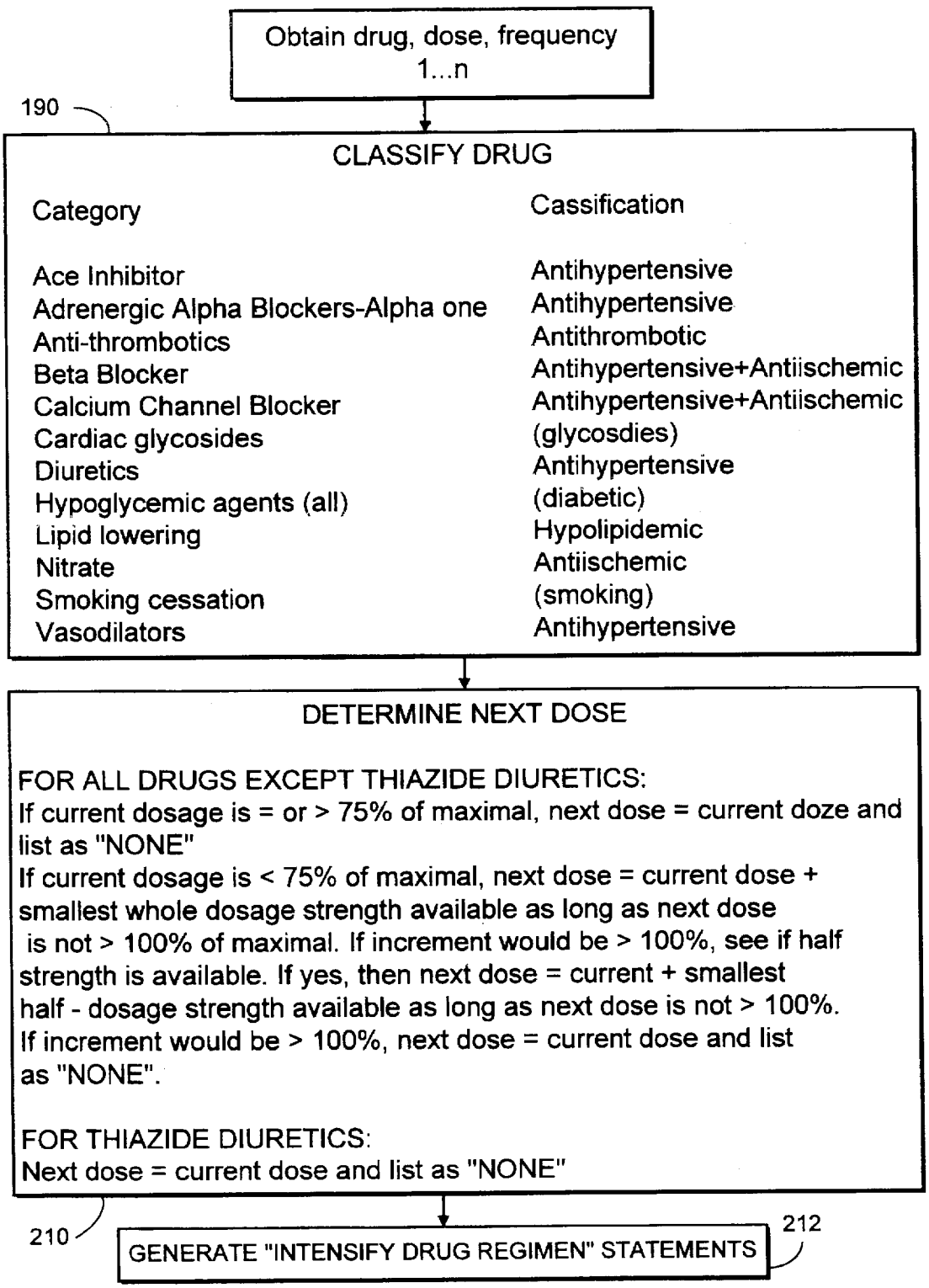
FIG. 5 is a block flow diagram of a drug classification algorithm used in conjunction with the preferred embodiment of the present invention.

The urgent positive ischemia algorithm of FIGS. 8A and 8B must be read in conjunction with box 210 of FIG. 5 which sets forth written parameters to determine when certain drugs should be increased or whether the current dose should be maintained. Depending on the parameters set forth in box 210, box 212 will generate the "intensify recommendation" boxes of FIGS. 8A and 8B.

In FIG. 8A, the first determination is whether hypertension is present (box 214). Information relating to hypertension is input into monitor 132 by the attending physician or other appropriate medical personnel. The decisions to be determined by the algorithm of FIGS. 8A and 8B include: (i) whether the patient has had a myocardial infarction, bypass surgery or angioplasty within the previous six months (box 216), (ii) whether the patient is presently taking any antischemic drugs (box 218), and (iii) whether patient is under 60 years of age. If the patient is on an antischemic drug (box 218), a determination is made whether the patient is on a beta blocker, a nitrate, a Ca antognist, or some combination thereof. Box 238 which indicates an error, occurs when a determination is made that a patient is on an antischemic drug but there has been a faulty determination in identifying the type of drug used. Ultimately, a preferred combination of drugs is achieved based on the algorithm of FIGS. 8A and 8B.

It will be noted with reference to FIG. 3, that when an "intensify recommendation" message is achieved based upon the algorithm of 8A and 8B, the cardiology consultation service 240 may be contacted. The cardiology consultation service 240 can be located at centralized data management center 122 or at a specialist's office 124. This consultation with a specialist is desirable when ischemia is present for more than 60 minutes based on known research which has validated the presence of ischemia as an accurate predictor of serious coronary events. If the report printed by the algorithm of FIGS. 8A and 8B is deemed accurate by the cardiology consultation service 240, the final report generation routine is run (box 242), and the written report is ultimately sent back to the office of the primary care physician (box 244).

In FIG. 3, it can also be seen that when ischemia of less than 60 minutes is detected or no ischemia is detected, the algorithm of FIG. 4 can be run and the final report can be generated and sent directly to the primary care physician's office 120. Optionally, cardiology consultation service 240 can be called upon to confirm the generated report of the algorithm of FIG. 4.

The coronary wellness master algorithm of FIG. 4 will now be described in detail. However, it will be noted by those skilled in the art that this algorithm, as well as all other algorithms described herein, are exemplary and represent the presently known best mode of incorporating the present invention. However, numerous variations can be incorporated yet still fall within the spirit and scope of the present invention.

First, it will be noted that the algorithm of FIG. 4 is run either after the negative ischemia algorithm of FIG. 6 or the positive ischemia algorithm of FIG. 7. FIG. 4 has seven branches which will be individually addressed below.

However, before addressing each of these seven factors, it should be noted that a final written recommendation for each factor will be generated to comprise a portion of the final written comprehensive management and prognosis report (box 242) and sent to the office of the primary care physician, if that is where the patient is located (box 244). A sample report which considers all seven factors plus ischemia therapy is shown in FIGS. 25A and 25B.

Figure 9:
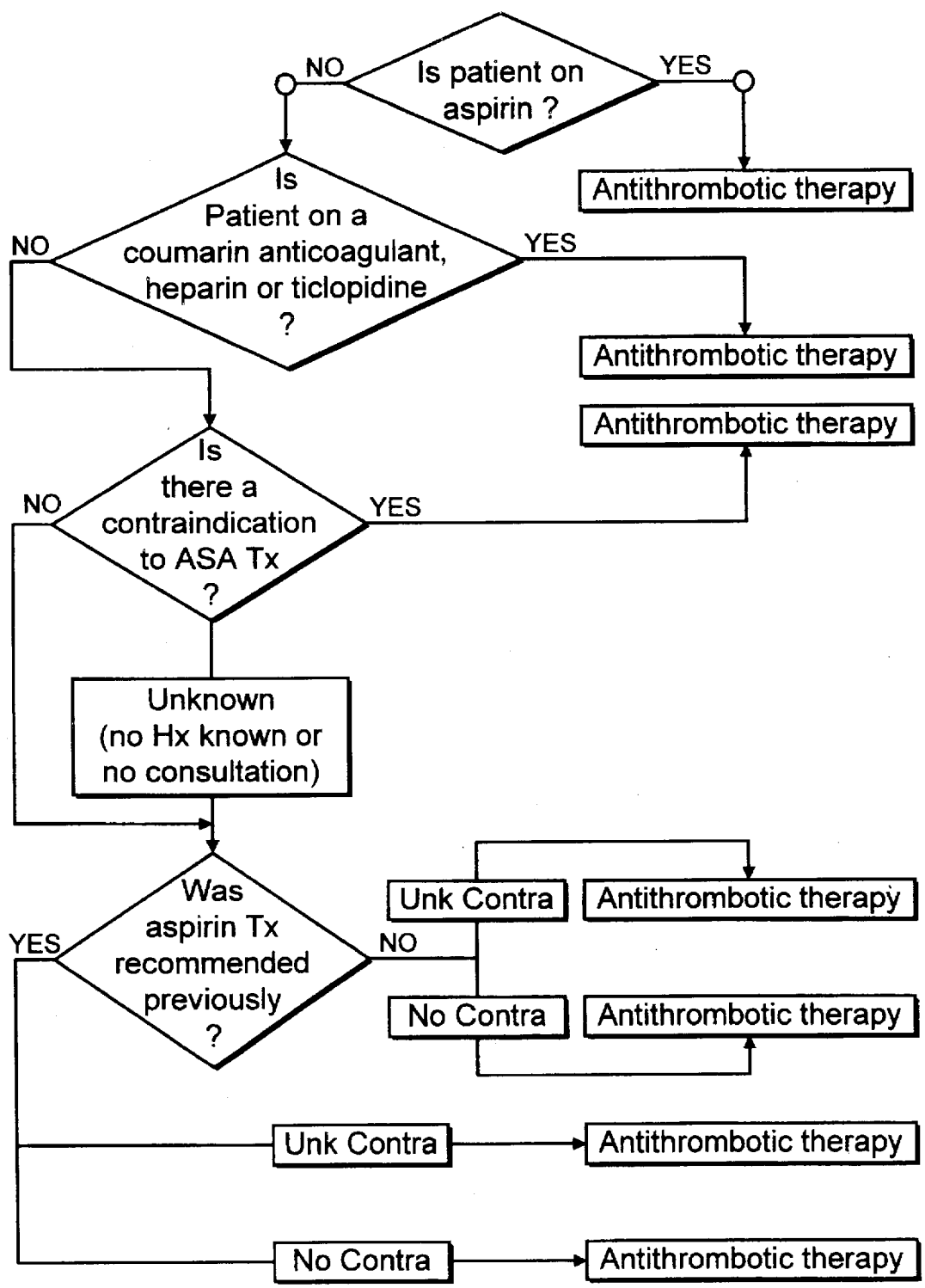
FIG. 9 is an antithrombosis algorithm used in conjunction with the preferred embodiment of the present invention.

An antithrombosis algorithm (box 246) and a recommendation with regard to antithrombosis therapy (box 248) is represented in FIG. 9. The factors to be considered when recommending an appropriate anti-thrombotic therapy includes information regarding whether the patient is on an anti-coagulant, heparin, or ticlopidine and also whether or not the patient is allergic to aspirin therapy. It should be noted that in this instance, and throughout the present invention, the actual written words for the antithrombotic therapy is not shown since the language can be customized by the user. What is important is that the present invention considers such factors, in the form of data, when automatically generating a final written report.

Figure 10A:
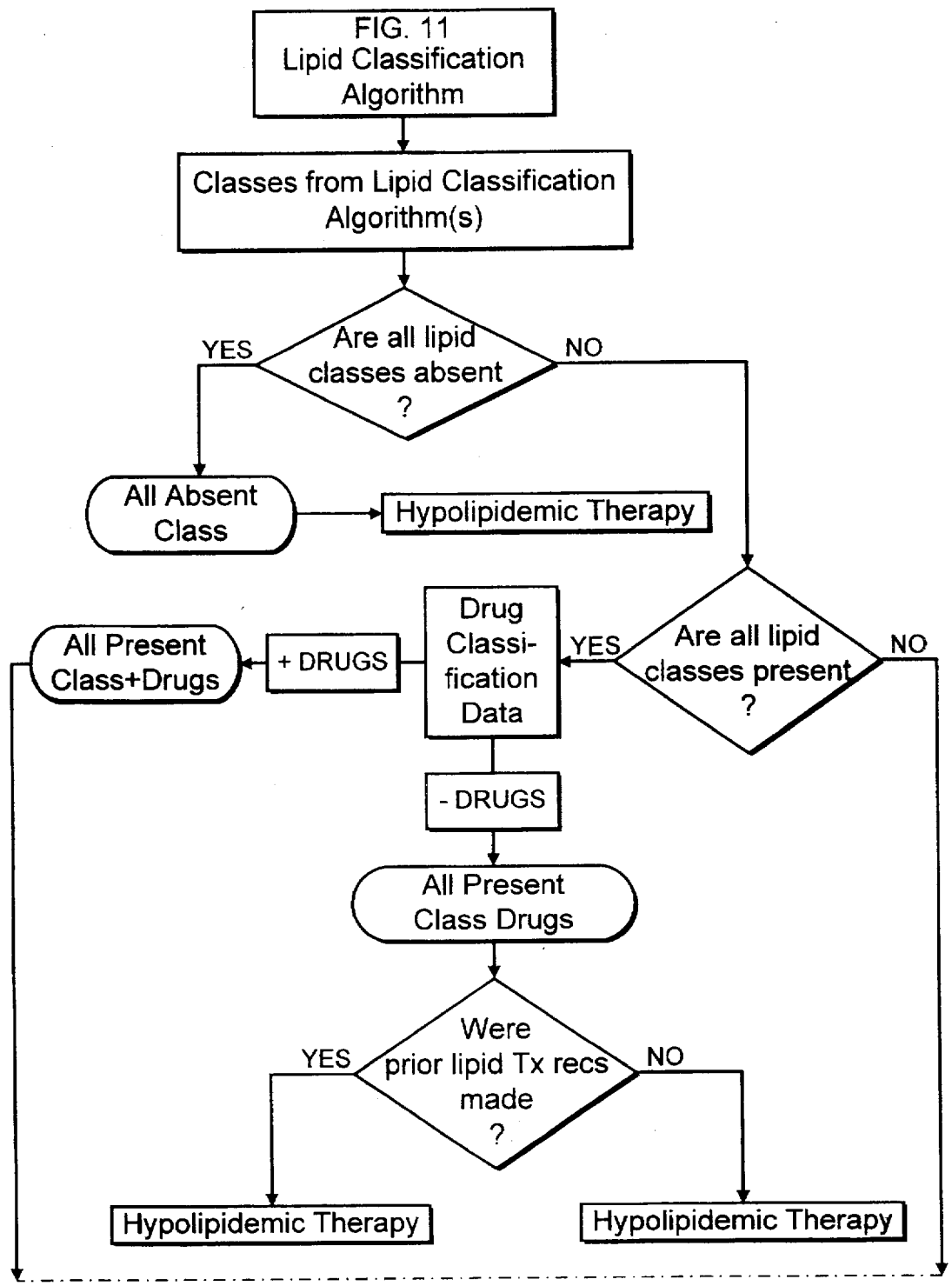
FIGS. 10A and 10B represent a block flow diagram of a lipid algorithm used in conjunction with the preferred embodiment of the present invention.
Figure 10B:
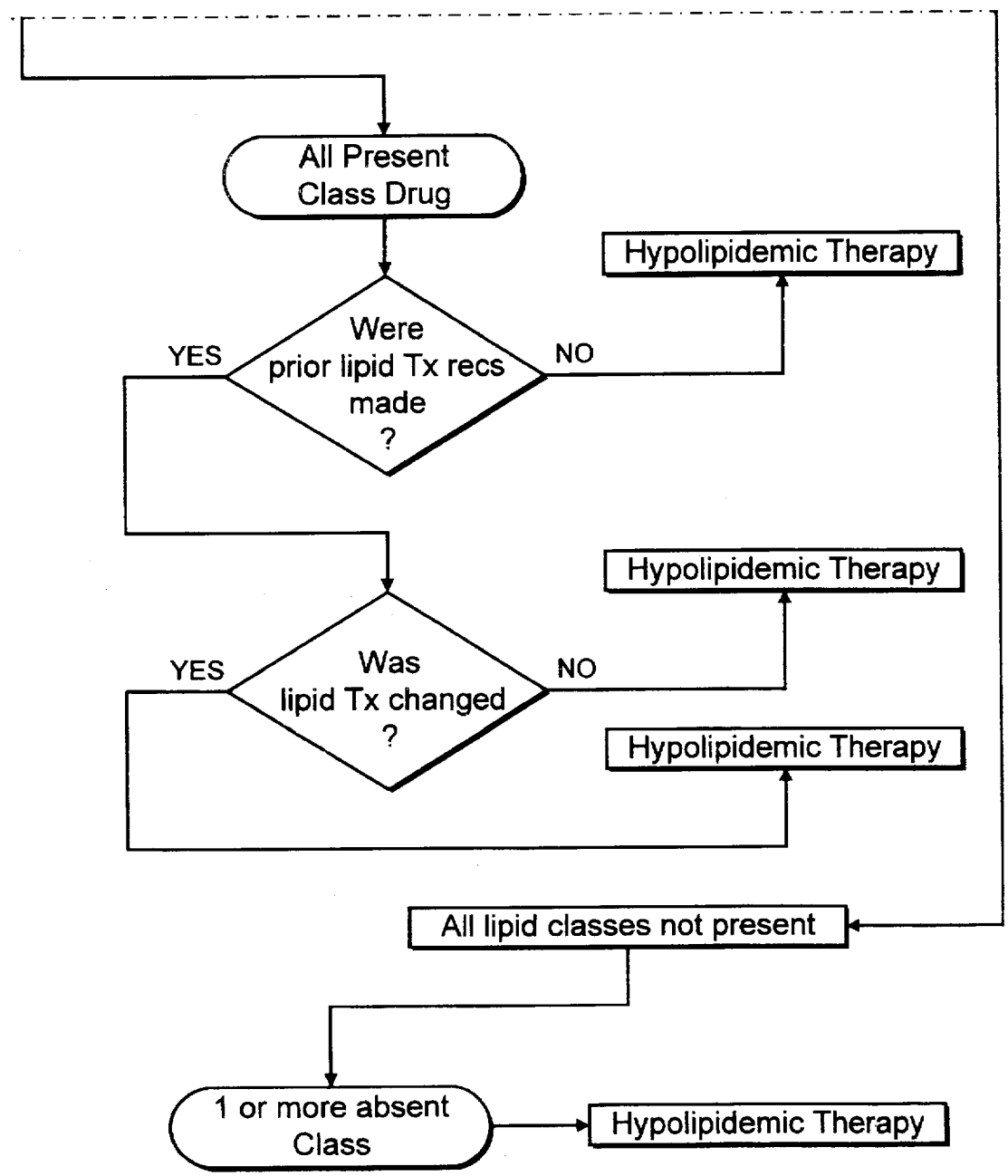
Figure 11:
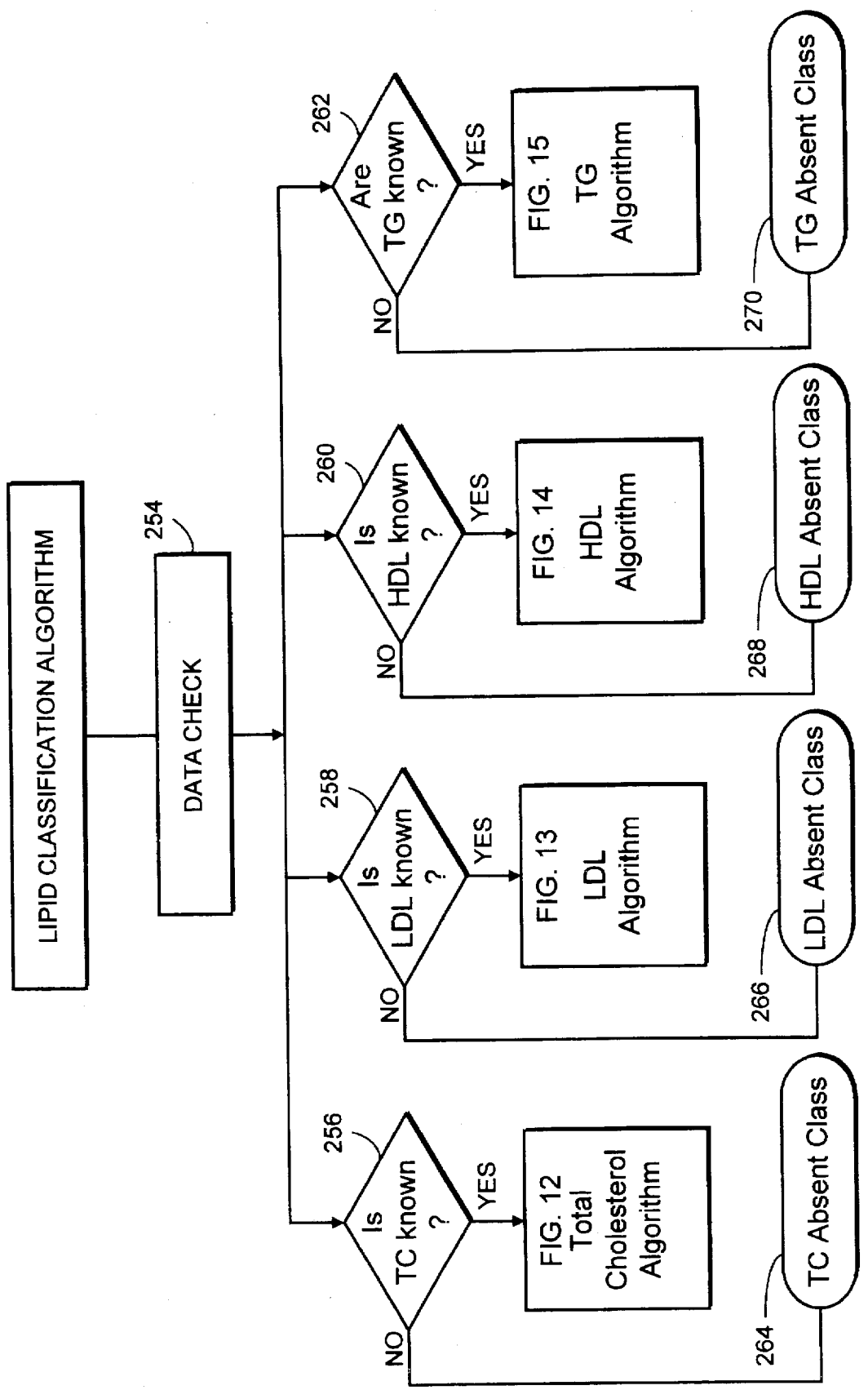
FIG. 11 is a block flow diagram of a lipid classification algorithm used in conjunction with the preferred embodiment of the present invention.
Figure 12:
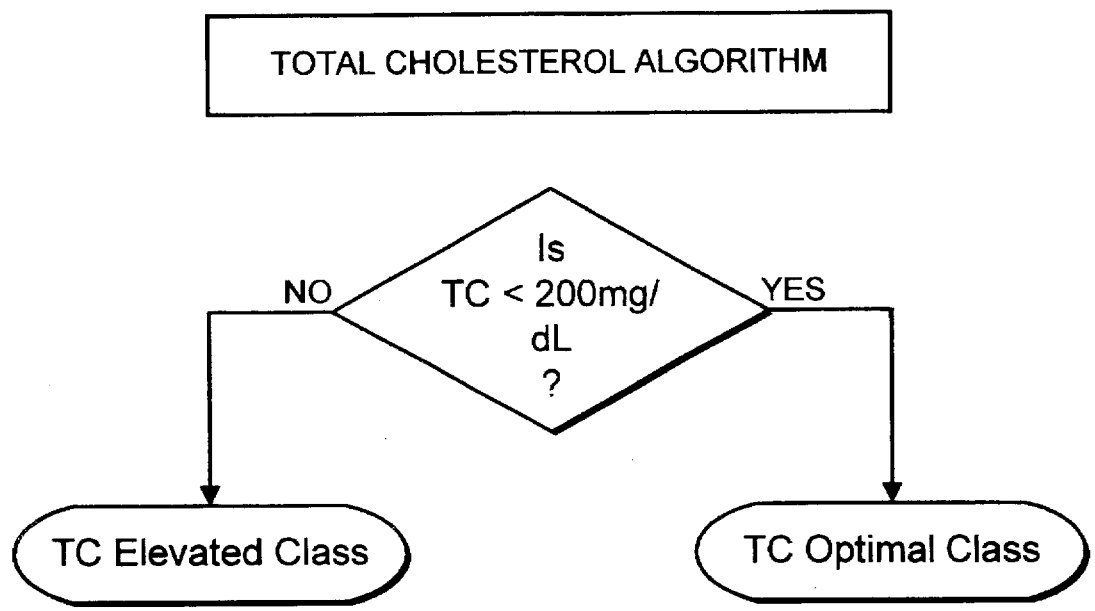
FIG. 12 is a block flow diagram of a total cholesterol algorithm used in conjunction with the preferred embodiment of the present invention.
Figure 13:
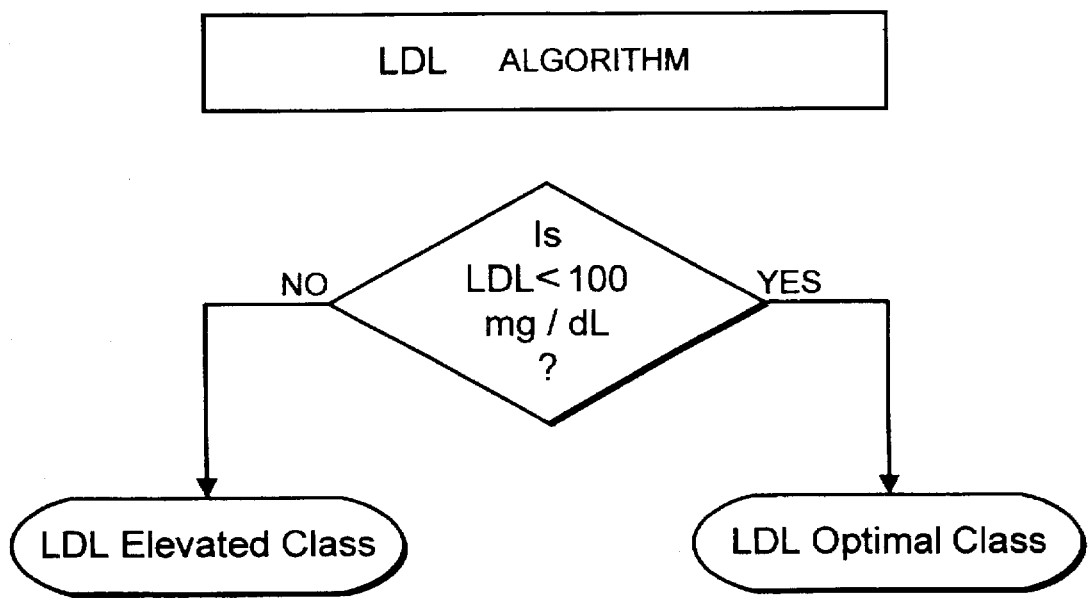
FIG. 13 is a block flow diagram of an LDL cholesterol algorithm used in conjunction with the preferred embodiment of the present invention.
Figure 14:
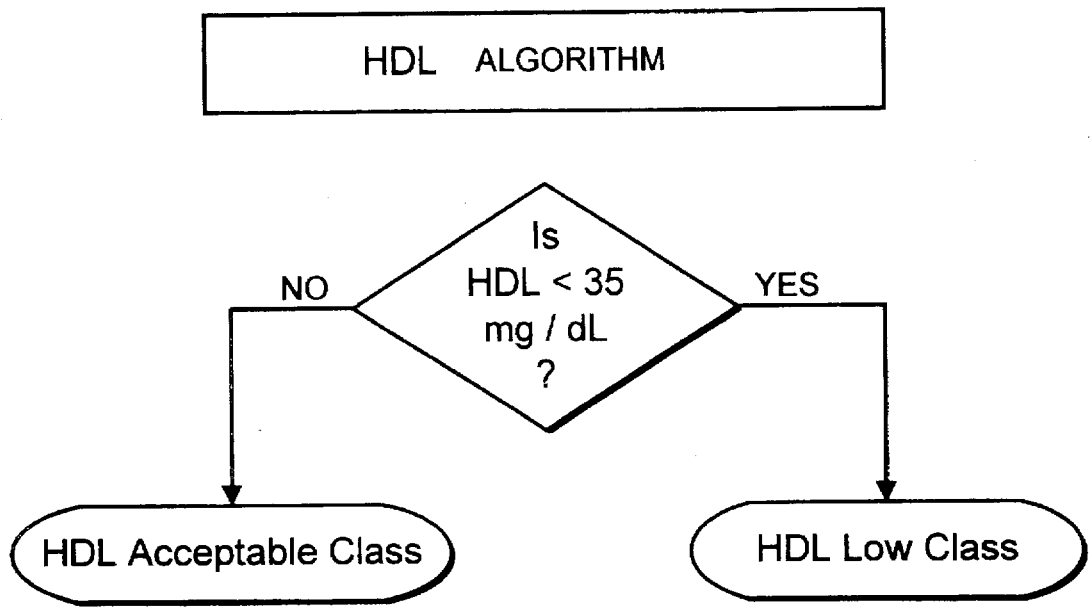
FIG. 14 is a block diagram of an HDL cholesterol algorithm used in conjunction with the preferred embodiment of the present invention.
Figure 15:
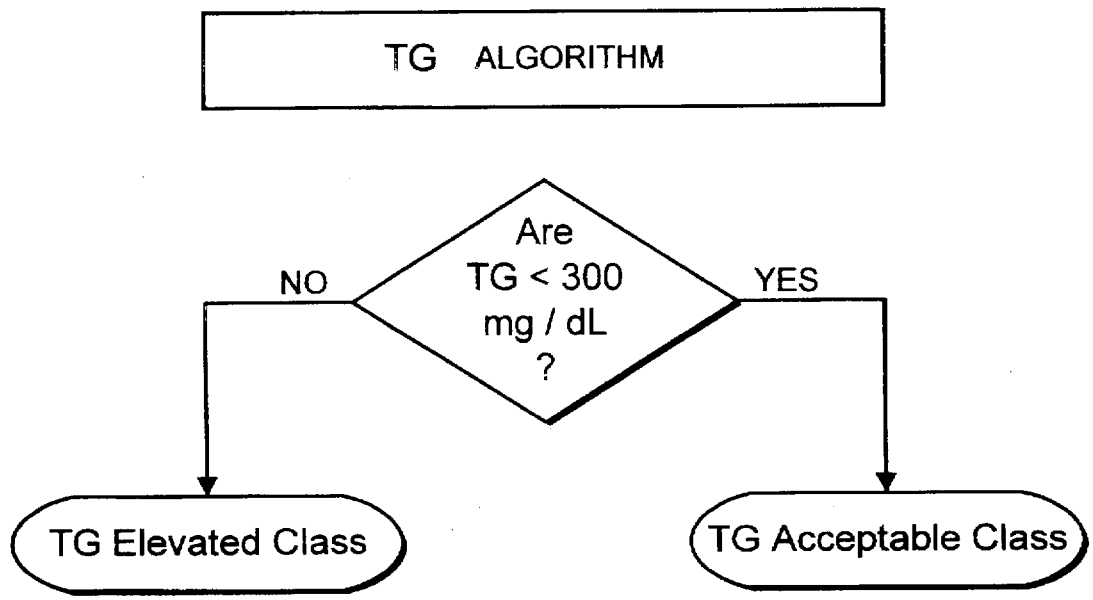
FIG. 15 is a block flow diagram of a triglycerides (TG) algorithm used in conjunction with the preferred embodiment of a present invention.

The second branch of the algorithm of FIG. 4 pertains to a lipid algorithm (box 250) and a recommended hypolipidemic therapy (box 252). This factor is considered in FIGS. 10–16. The lipid algorithm of FIGS. 10A and 10B first instructs the computer to run the lipid classification algorithm of FIG. 11. In FIG. 11, a data check, indicated by box 254, is first run. If total cholesterol is known (box 256) a total cholesterol algorithm of FIG. 12 is run to classify the patient into either a total cholesterol elevated class or a total cholesterol optimal class. In FIG. 12, the upper limit for normal total cholesterol is set at 200 mg/dL. Next, the lipid classification algorithm checks to see if LDL cholesterol is known (box 258). If a value for this factor is known, the LDL cholesterol algorithm of FIG. 13 is run in order to classify the patient into either an LDL elevated class or an LDL optimal class. In this instance, the LDL upper limit is set at 100 mg/dL. Next, the lipid classification algorithm determines if HDL cholesterol is known. If this value is known for the patient being evaluated, the HDL cholesterol algorithm of FIG. 14 is run to classify a patient into either an HDL cholesterol acceptable class or a HDL cholesterol low class. The HDL lower limit is set in FIG. 14 at 35 mg/dL. Finally, a determination is made whether a triglyceride level is known for the patient (box 262). If so, the algorithm of FIG. 15 is run in order to classify the patient into either a TG elevated class or a TG acceptable class. The TG upper level is set at 300 mg/dL in FIG. 15.

It should be understood that the acceptable levels set forth in FIGS. 12–15 can be modified based either on other known information about the patient or varying acceptable levels established by doctors based on empirical data. If the total cholesterol level is unknown, message 264 is generated to advise the treating physician to provide such information if known or to ascertain (then report) the missing TC level. Similarly, if LDL cholesterol is not known, a report requesting such information (box 266) is generated; if HDL cholesterol level is not known, a report requesting this information is made (box 268); and if the level of triglycerides is unknown, a report requesting this information (box 270) is generated.

Figure 16A:
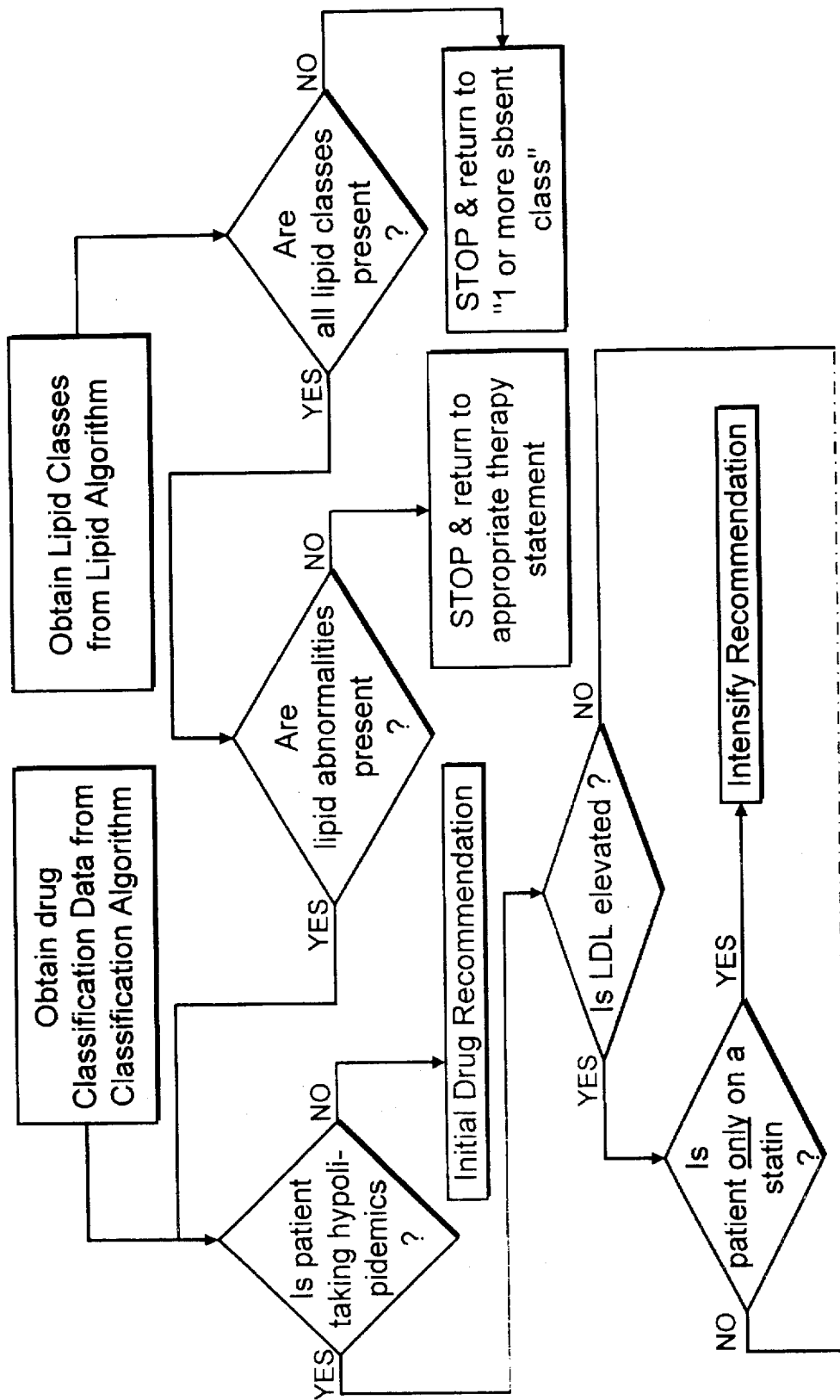
FIGS. 16A, 16B and 16C represent a block flow diagram of a hypolipidemic therapy algorithm used in conjunction with the preferred embodiment of the present invention.
Figure 16B:
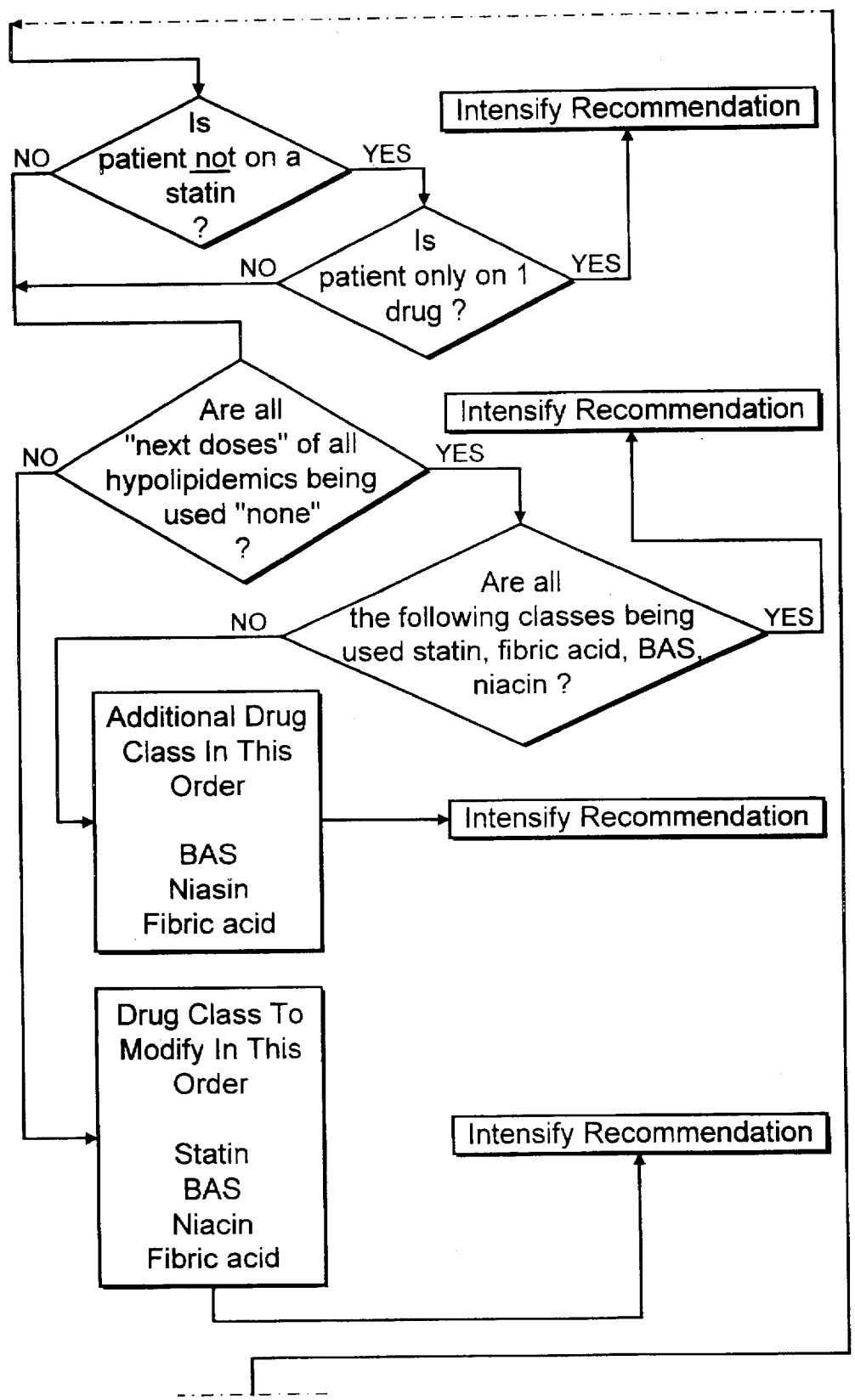
Figure 16C:
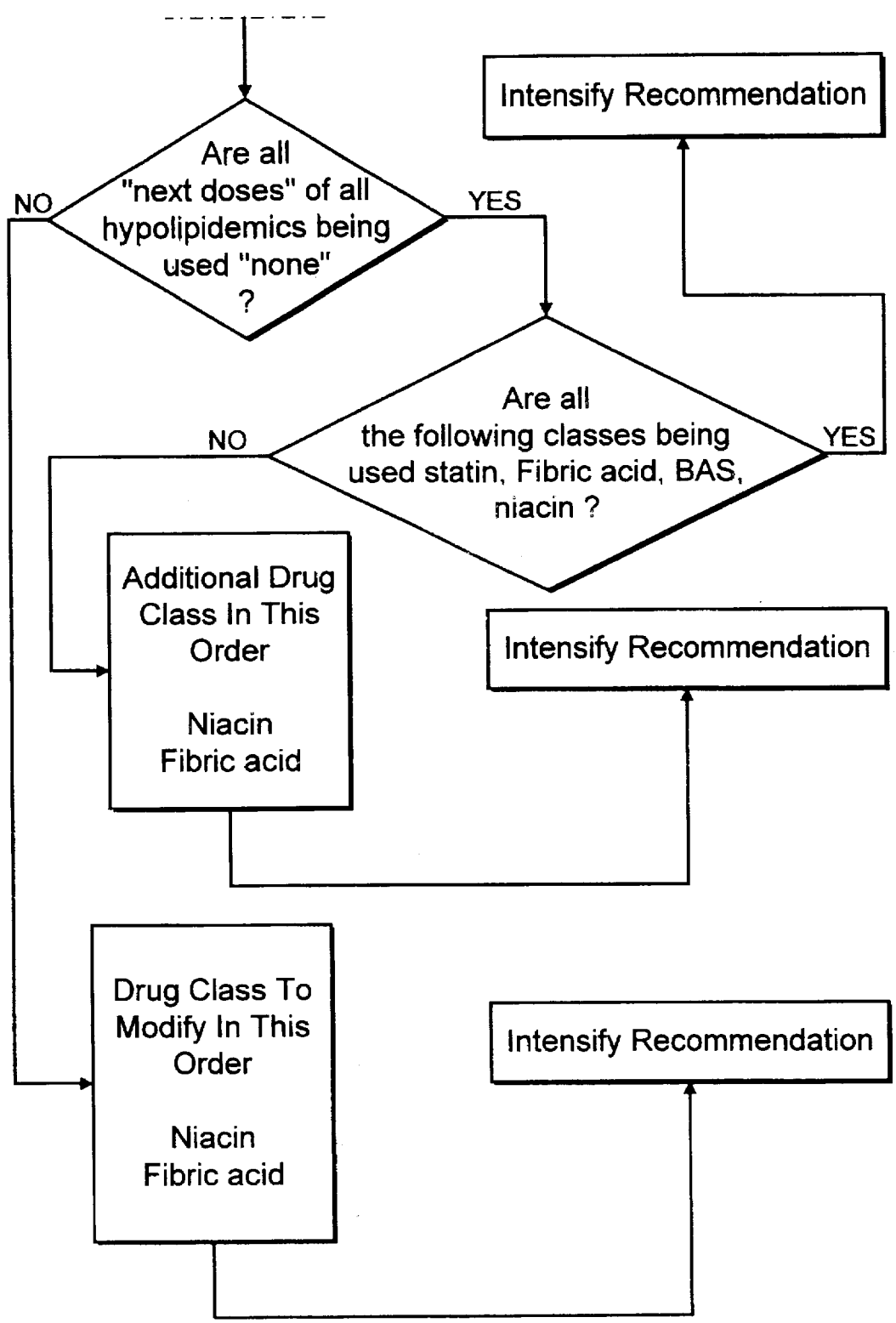

Once the necessary lipid levels are known, the algorithm of FIGS. 16A, 16B and 16C is run. Again, this hypolipidemic therapy algorithm will not be described in detail since it is only exemplary in nature. However, the flow chart provided is self-explanatory.

Figure 17A:
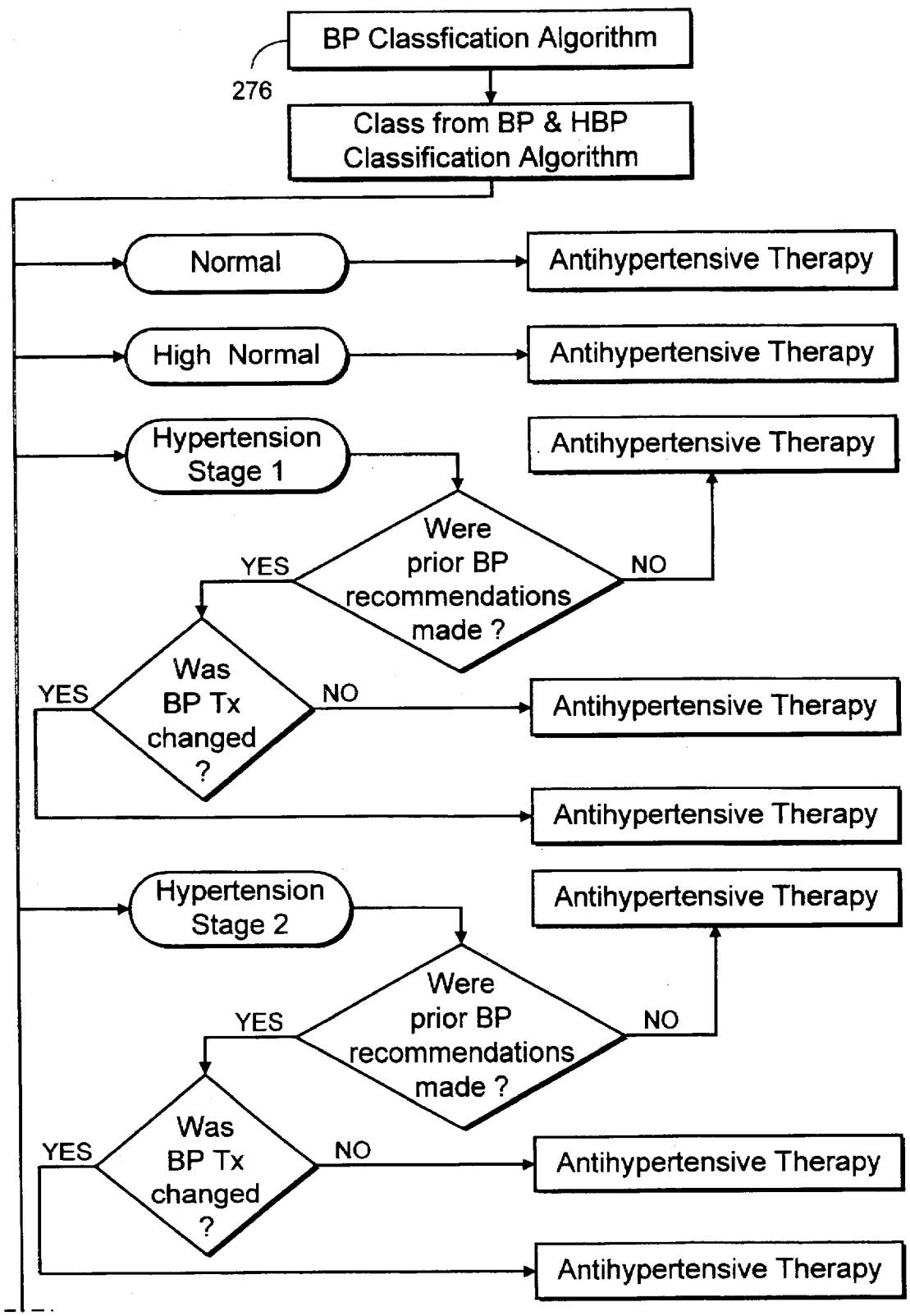
FIGS. 17A and 17B represent a block flow diagram of a hypertension algorithm used in conjunction with the preferred embodiment of the present invention.
Figure 17B:
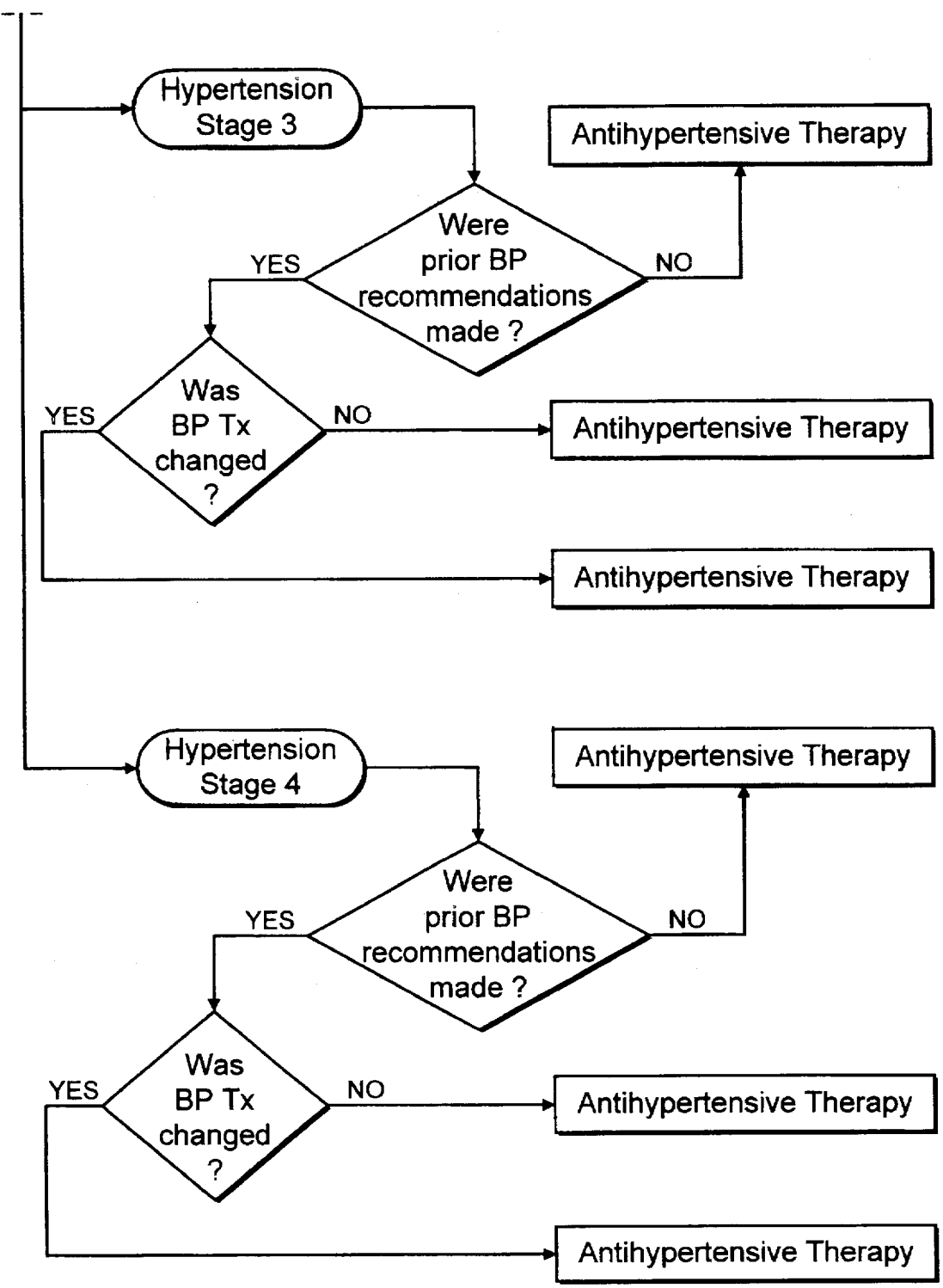

Next, in the coronary wellness master algorithm of FIG. 4, a blood pressure (or hypertension) algorithm 272 is run and an appropriate therapy (box 274) is also formulated. This branch of the algorithm is reflected in FIGS. 17–20. It should also be noted that this hypertension algorithm can be used to supply information to box 214 of the urgent positive ischemia algorithm of FIGS. 8A and 8B. The first step in the algorithm of FIG. 17 is to run the blood pressure classification algorithm of FIG. 18. Before beginning with the description of FIG. 18, it should be noted that unlike the lipid algorithm, wherein the levels of total cholesterol, LDL cholesterol, HDL and triglycerides levels are basically determined to be acceptable or not (i.e., there are two levels), blood pressure will have six classifications. These six classifications are: normal, high-normal, mild hypertension (class 1), moderate hypertension (class 2), severe hypertension (class 3), and very severe hypertension class 4). As implied by their names, class 4 hypertension ms certainly of a more immediate concern than class 1 hypertension.

Figure 18:
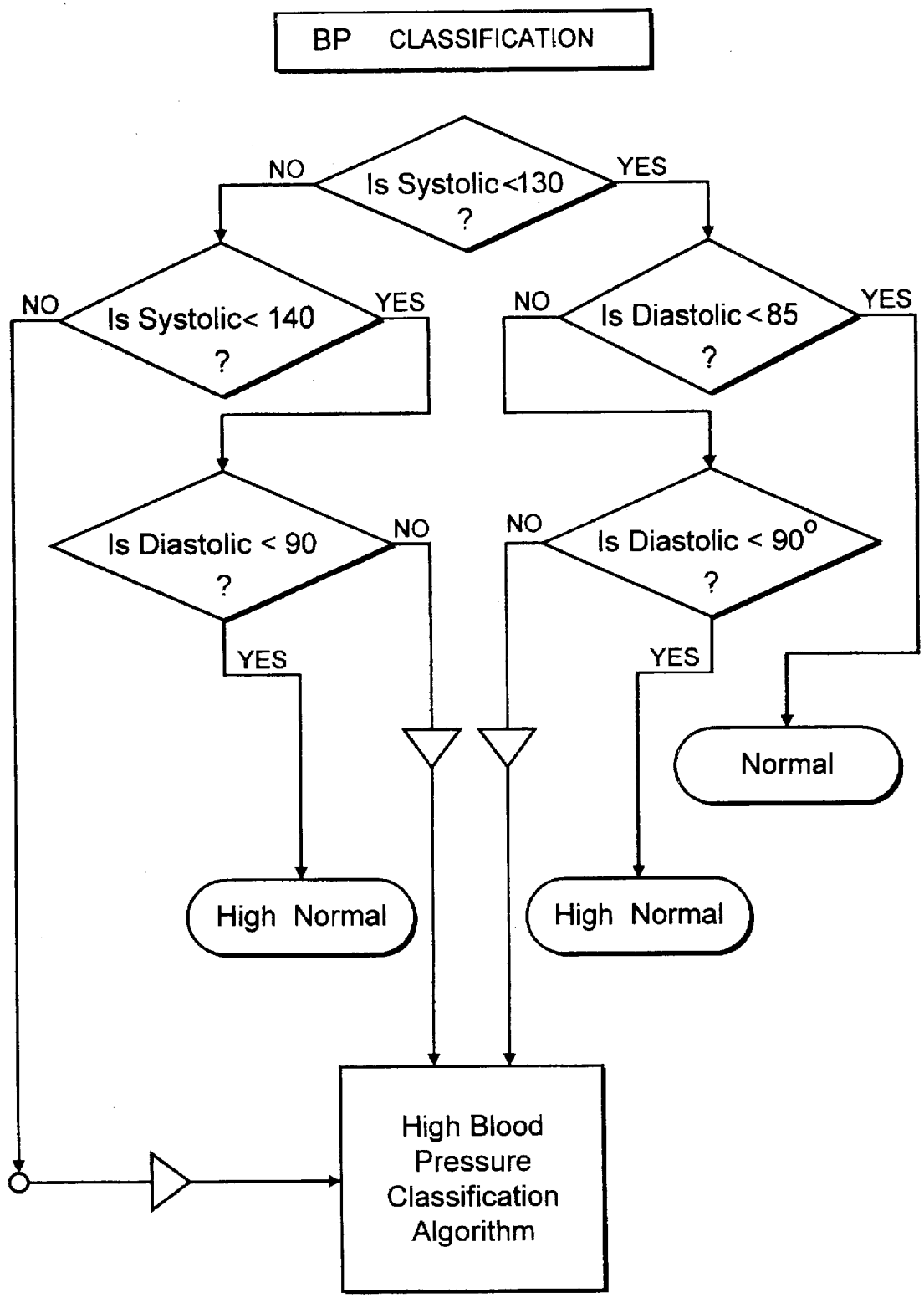
FIG. 18 is a block flow diagram of a blood pressure classification algorithm used in conjunction with the preferred embodiment of the present invention.
Figure 19:
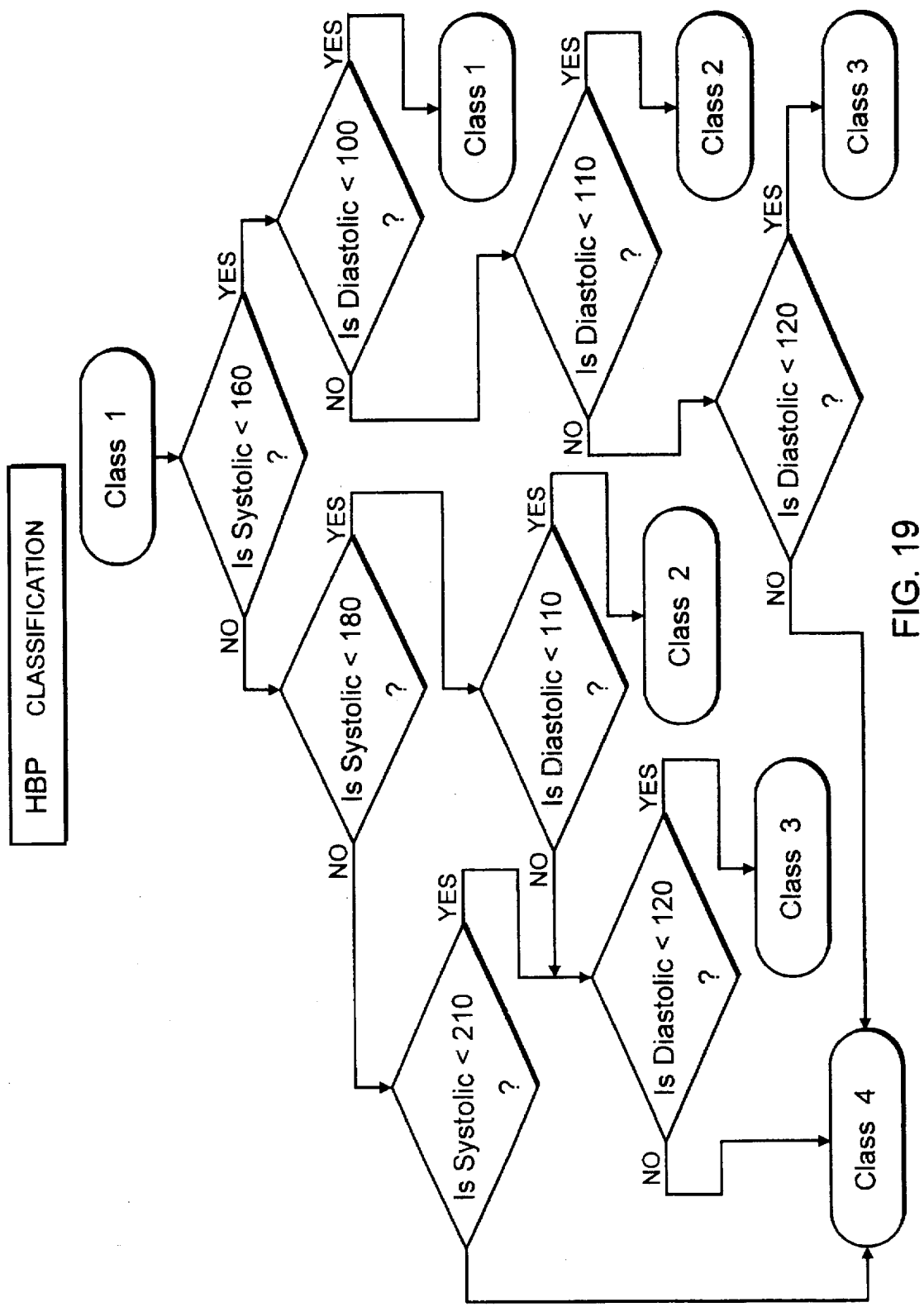
FIG. 19 is a block flow diagram of a high blood pressure (HBP) classification algorithm used in conjunction with the preferred embodiment of the present invention.

The first step in determining into which of the six classifications of blood pressure the patient falls is made by software described in the block flow diagram of FIG. 18. If systolic pressure is under 130 and diastolic pressure is under 85, the patient is described as having normal blood pressure. Alternatively, if systolic pressure is under 130, but diastolic pressure is between 85 and 90, the patient is described as having a high normal blood pressure classification. Similarly, if systolic pressure is between 130 and 140, and diastolic pressure is less than 90, the patient is also described as having a high normal blood pressure classification. Finally, if diastolic pressure is greater than 90 or systolic pressure is greater than 140, the patient will be described as having high blood pressure classification. To determine into which of the four classes of high blood pressure a patient falls, the algorithm of FIG. 19 is run. Since FIG. 19 is rather self-explanatory, it will not be described in detail herein. Furthermore, since the "base" numbers might vary, any detailed description of an easily understood flow diagram would be of very little value. In essence, the higher the measured pressures, the more severe the high blood pressure classification.

Figure 20:
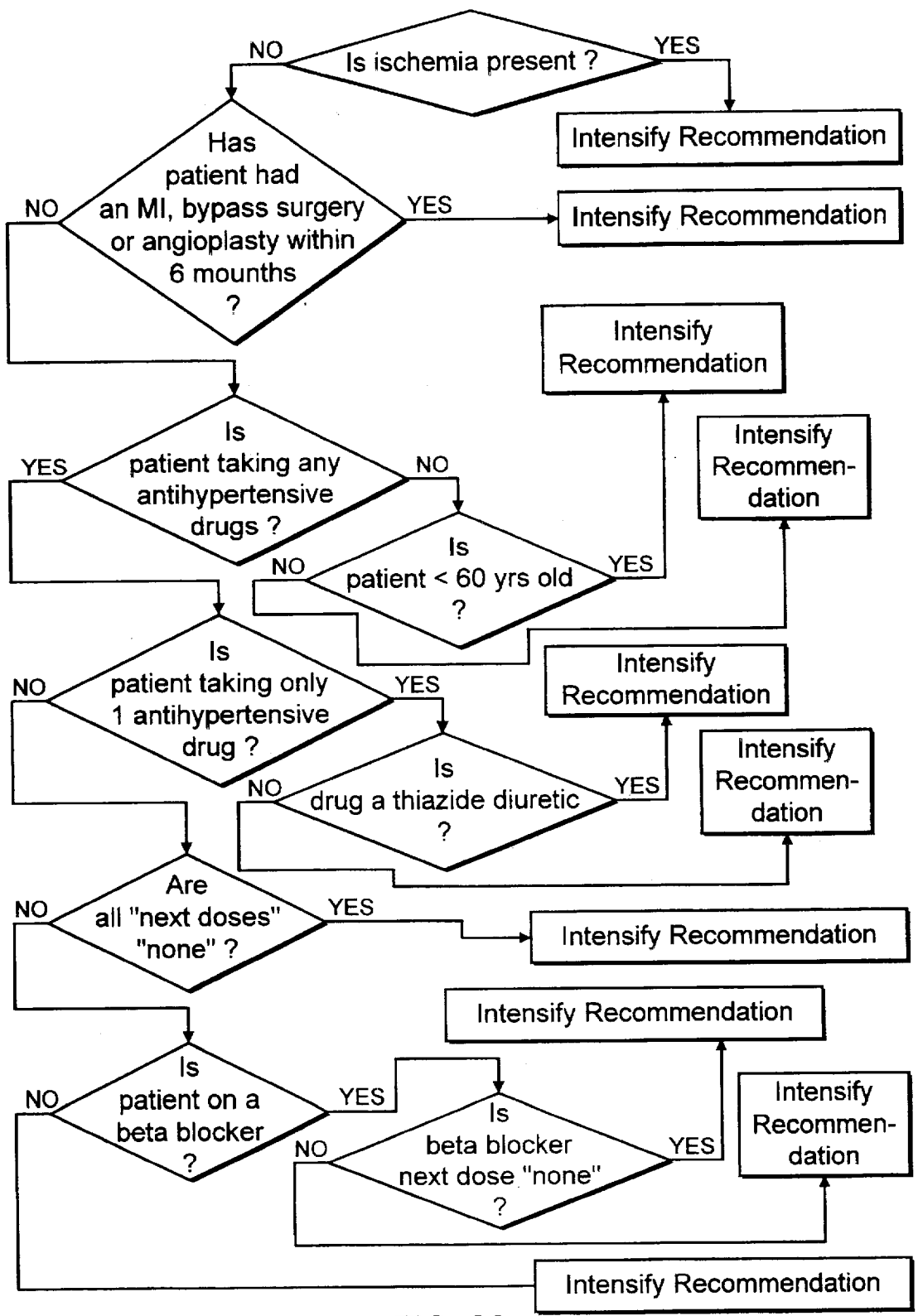
FIG. 20 is a block flow diagram of a hypertensive therapy algorithm used in conjunction with the preferred embodiment of the present invention.

The recommended treatment for each of the six classifications of blood pressure (box 274 of FIG. 4) is described in FIG. 20. Again, it should be noted that the written "intensify recommendation" messages on the right side of FIG. 19 are subject to customization by the user.

Figure 21:
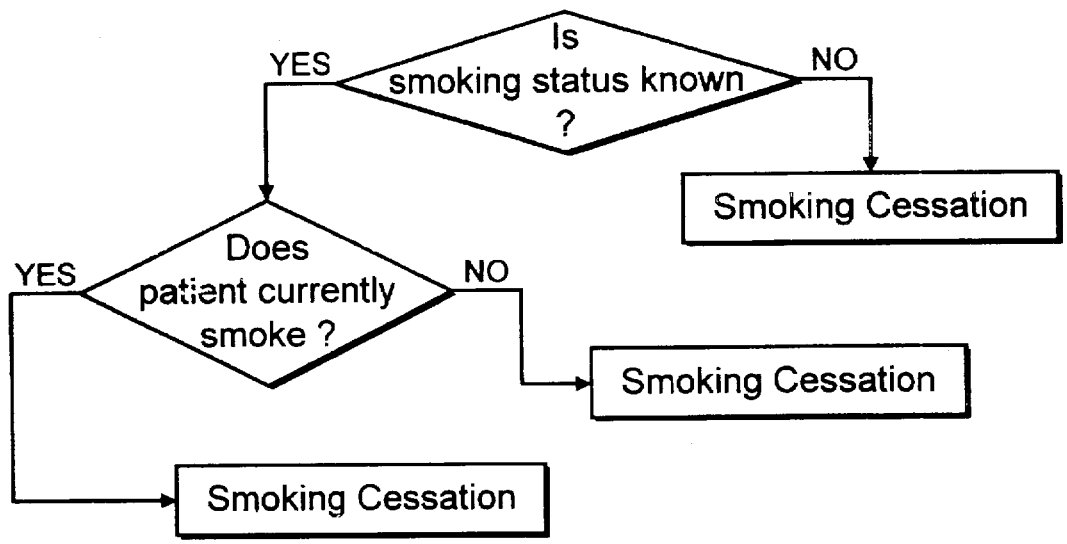
FIG. 21 is a block flow diagram of a diabetes algorithm used in conjunction with the preferred embodiment of the present invention.

The next branch of the coronary wellness master algorithm of FIG. 4 is the smoking cessation algorithm 278. Smoking cessation algorithm is reflected in FIG. 21. In essence, if the patient is not smoking, the "smoking cessation" therapy (box 280) will generally simply advise the treating physician to encourage the patient to continue not smoking. Alternatively, if the patient is currently smoking, the "smoking cessation" therapy algorithm might suggest use of a nicotine patch or may simply instruct the treating physician to encourage the patient to quit or at least reduce his smoking habit.

Figure 22:
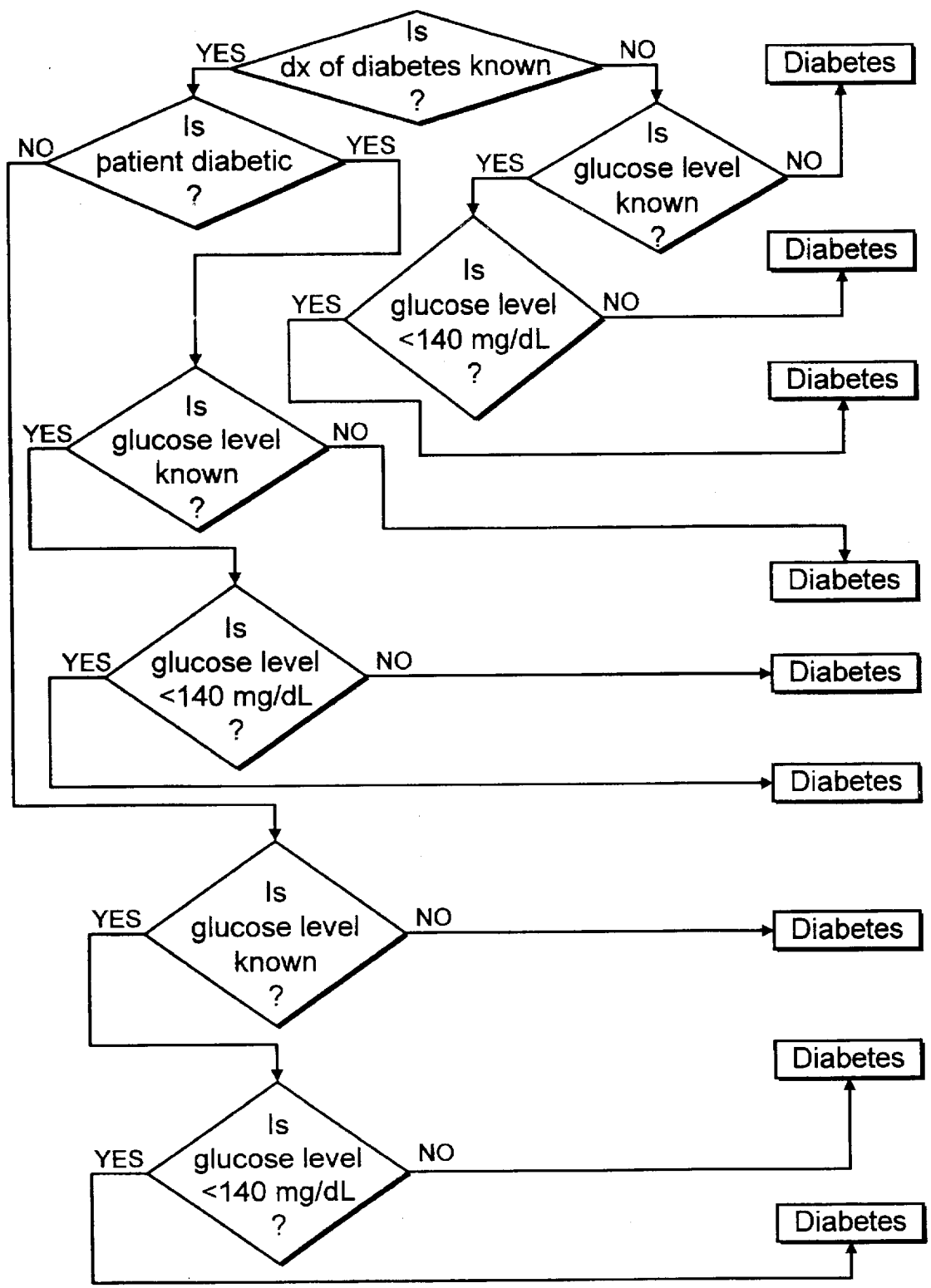
FIG. 22 is a smoking cessation algorithm used in conjunction with the preferred embodiment of the present invention.

The next branch of the coronary wellness master algorithm of FIG. 4 (box 282) concerns the patient's glucose level. Diabetes algorithm is shown in FIG. 22. The recommended hypoglycemic therapy (box 284) is determined based on the level of the patient's detected glucose level.

Figure 24:
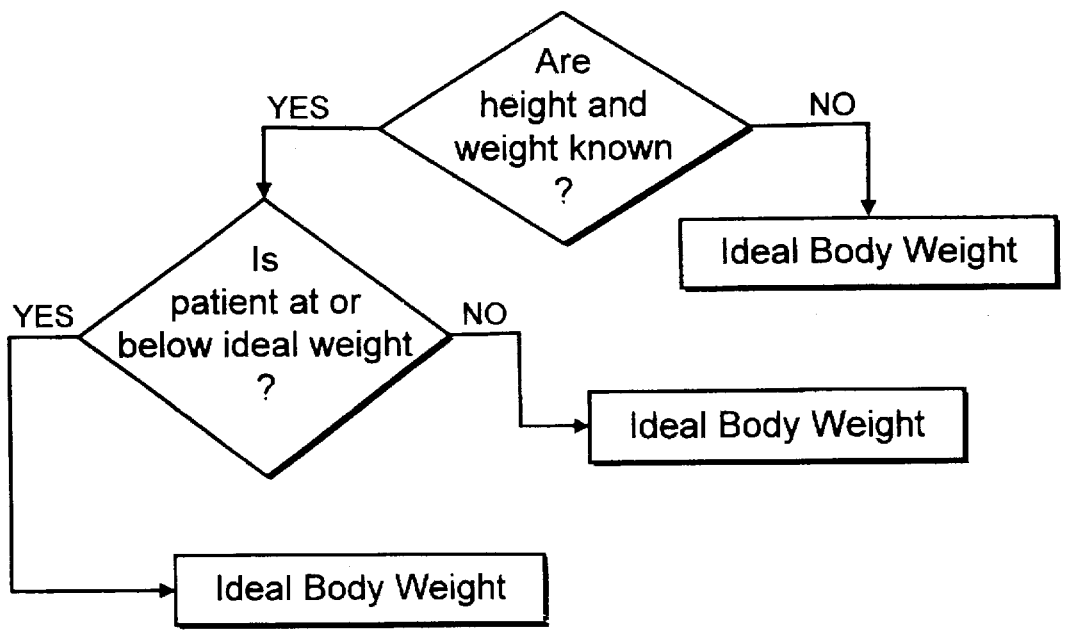
FIG. 24 is an obesity algorithm used in conjunction with the preferred embodiment of the present invention.
Figure 23:
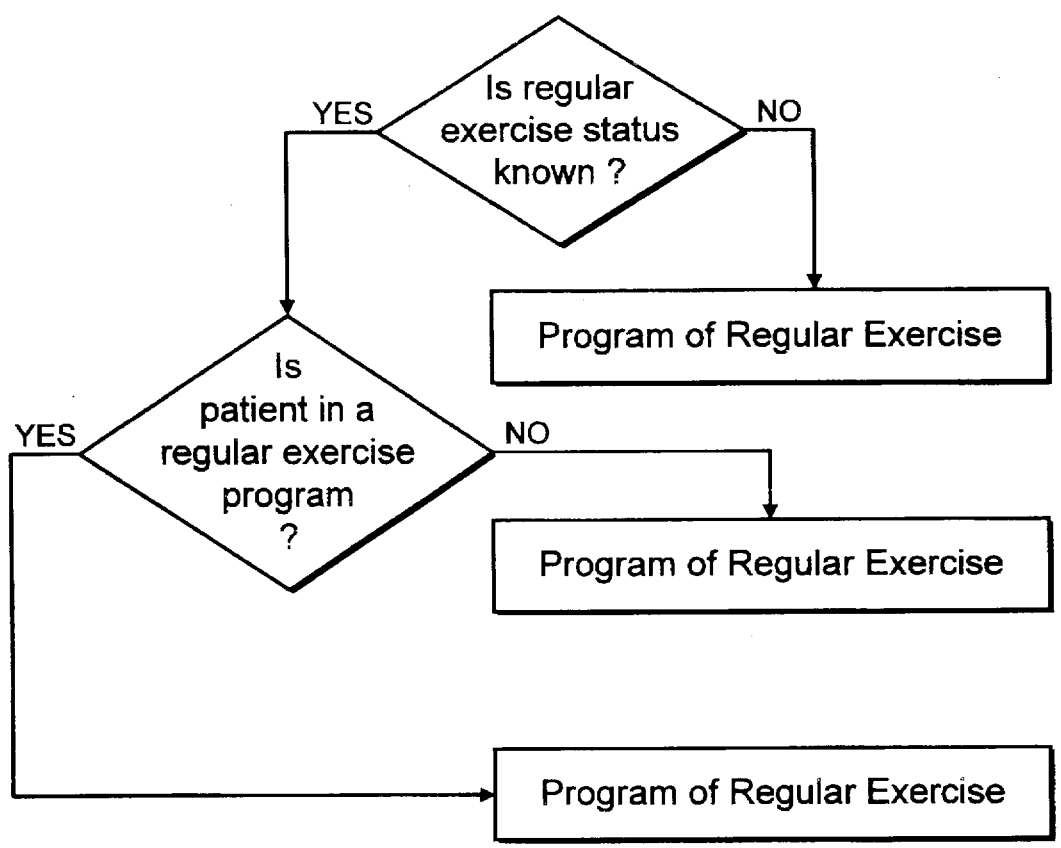
FIG. 23 is an exercise algorithm used in conjunction with the preferred embodiment of the present invention.

The next branch of the coronary wellness master algorithm of FIG. 4 relates to the exercise program that a patient is on and a recommended exercise program (boxes 286 and 288). The exercise algorithm is represented in the block flow diagram of FIG. 23. Finally, a last branch of the coronary wellness master algorithm of FIG. 4 relates to obesity (boxes 290 and 292). This algorithm is represented in the block flow diagram of FIG. 24.

The series of algorithms described to this stage appear complicated, but will result in a written report such as that shown in FIGS. 25A and 25B. In essence, the data provided to centralized data management center 122 can be correlated and analyzed to provide the written report of FIGS. 25A and 25B. It will be noted that written recommendations with regard to antischemic therapy, hypolipidemic therapy, antihypertensive therapy, antithrombotic therapy, diabetes, smoking cessation, body weight, and exercise have been generated. Thus, the present invention utilizes data from a remote location to provide a concise written comprehensive management and prognosis report which is automatically generated using "artificial intelligence".

Another advantage of the present invention is that summary reports can be printed which include all the data input into monitor 134. This written summary will eliminate the need for a doctor to write time consuming notes in the patient's file, or will at least provide a means to confirm whether such entries have been properly entered or read.

By using the novel system and method described herein, the treatment of coronary patients can be made in a manner which utilizes risk stratification to optimize therapy and minimize cost. It will be noted by those skilled in the art that while the best mode embodiment disclosed herein relates to coronary care, the overall novel system and method described can be used in conjunction with other types of disease management. Furthermore, a visit to a primary care physician's office is not even necessary, and instead a diagnosis can be made and provided to the patient in his/her own home, particularly by supplying the patient with a buffer interface module or a location where a buffer interface module exists. Furthermore, other factors which might impact treatment may also be recorded and passed along to the centralized data management center. A written report can be provided with regard to such factors.

Thus, while there has been shown and described what is presently considered to be the preferred embodiment of this invention, it will be apparent to those skilled in the art that various changes and modifications may be made without departing from the broader aspects of this invention. It is, therefore, aimed in the appended claims to cover all such changes and modifications as fall within the spirit and scope of the invention.

We claim:

1. A system at a centralized data management center for a patient at a remote location, comprising:

means for converting information regarding a condition of said patient into data;

a first telecommunications means for transferring said data to said centralized data management center from said remote location; and processing means at said centralized data management center for receiving said data and for automatically generating an alpha-numeric comprehensive management and prognosis report including a specific therapy for said patient based on analysis of said data wherein said comprehensive management and prognosis report is indicative of one of a first class wherein said report is non-reflective of a serious medical condition and a second class wherein said report is reflective of a serious medical condition whereby, when report falls within said second class, said data is reviewed and confirmed by a specialist.

2. The system of claim 1 further comprising:
a second telecommunications means for transferring said comprehensive management and prognosis report to said remote location from said centralized data management center.

3. The system of claim 1 further comprising:
storage means at said centralized data management center for maintaining a record of said comprehensive management and prognosis report.

4. The system of claim 3 further comprising:
means for providing access to said storage means.

5. The system of claim 1 wherein said data includes information reflective of an ECG signal of said patient.

6. The system of claim 5 wherein said serious medical condition is ischemia.

7. The system of claim 1 wherein said processing means considers at least one risk factor which has been established based on empirical data in generating said comprehensive management and prognosis report.

8. The system of claim 1 wherein said processing means considers known health-related information about said patient in generating said comprehensive management and prognosis report.

9. A method performed at a centralized data management center for a patient at a remote location, comprising the steps of:
converting information regarding a condition of said patient into data;
transferring said data to said centralized data management center from said location;
generating an alpha-numeric comprehensive management and prognosis report including a specific therapy for said patient at said centralized data management center based on analysis
characterizing said comprehensive management and prognosis report as indicative of one of a first class wherein said report is non-reflective of a serious medical condition and a second class wherein said report is indicative of a serious medical condition; and
forwarding said data to a specialist for review and confirmation when said report falls within said second class.

10. The method of claim 9 further comprising the step of:
transferring said comprehensive management and prognosis report to said remote location from said centralized data management center.

11. The method of claim 9 further comprising the step of:
storing said comprehensive management and prognosis report at said centralized data management center.

12. The method of claim 9 further comprising the step of:
storing said data at said centralized data management center.

13. The method of claim 9 whereby said step of generating said comprehensive management and prognosis report includes the step of considering at least one risk factor established based on empirical data.

14. The method of claim 9 whereby said step of generating said comprehensive management and prognosis report includes the step of considering known health-related information about said patient.

15. The system of claim 9 wherein said data includes information reflective of an ECG signal of said patient.

16. The system of claim 15 wherein said serious medical condition is ischemia.

17. A system at a centralized data management center for a patient at a remote location based on a plurality of health risk factors, said system comprising:
means for establishing data reflective of said health risk factors; and
processing means at said centralized data management center for receiving and interpreting said data and for automatically generating an alpha-numeric comprehensive management and prognosis report including a specific therapy for said patient based on said plurality of health risk factors wherein said comprehensive management and prognosis report is indicative of one of a first class wherein said report is non-reflective of a serious medical condition and a second class wherein said report is reflective of a serious medical condition whereby, when report falls within said second class, said data is reviewed and confirmed by a specialist.

18. The system of claim 17 wherein one of said plurality of health risk factors is myocardial ischemia.

19. A method performed at a centralized data management center for a patient at a remote location based on a plurality of health risk factors, said method comprising the steps of:
establishing data reflective of said health risk factors;
processing said data at said centralized data management center;
generating an alpha-numeric comprehensive management and prognosis report including a specific therapy for said patient by selecting stored written messages based on said processing step:
characterizing said comprehensive management and prognosis report as indicative of one of a first class wherein said report is non-reflective of a serious medical condition and a second class wherein said report is indicative of a serious medical condition; and
forwarding said data to a specialist for review and confirmation when said report falls within said second class.

20. The method of claim 19 further comprising the step of:
transmitting said alpha-numeric comprehensive management and prognosis report from said centralized data management center to said remote location.

21. The method of claim 19 further comprising the step of:
storing said comprehensive management and prognosis report in a memory means at said centralized data management center.

22. The method of claim 21 further comprising the step of:
providing access to said memory means.

23. A system of disease risk stratification performed at a centralized data management center for a patient located at a first remote location into a first class whose medical condition requires consultation with a specialist located at a second remote location and a second class whose medical condition can be treated without consultation of said specialist, said system comprising:
first telecommunication means at said centralized data management center for receiving data representative of a condition of said patient from said first remote location;
processing means at said centralized data management center for interpreting said data and for automatically generating a comprehensive management and prognosis report for determining whether said data reflects whether said patient falls within said first class or said second class of individuals;
storage means at said centralized data management center providing diagnostic and treatment alpha-numeric messages to said first remote location when said patient falls within said second class; and forwarding said data to said second remote location for interpretation by said specialist when said patient falls within said first class.

24. A method of disease risk stratification performed at a centralized data management center for a patient located at a first remote location into a first class whose medical condition requires consultation with a specialist located at a second remote location and a second class whose medical condition can be treated without consultation of said specialist, said system comprising:

receiving data representative of a condition of said patient from said first remote location;

automatically generating a comprehensive management and prognosis report for determining whether said data reflects whether said patient falls within said first class or said second class of individuals;

providing diagnostic and treatment alpha-numeric messages to said first remote location when said patient falls within said second class; and forwarding said data to said second remote location for interpretation by said specialist when said patient falls within said first class.

* * * * *